(12) United States Patent
Miller et al.

(10) Patent No.: US 8,418,288 B2
(45) Date of Patent: Apr. 16, 2013

(54) MODULAR PATIENT SUPPORT SYSTEM

(75) Inventors: Daniel W. Miller, Oriental, NC (US);
Steve K. McAllaster, Rancho Cucamonga, CA (US); Jerry D. Slater, Redlands, CA (US); Nickolas S. Rigney, Redlands, CA (US); Daniel C. Anderson, Loma Linda, CA (US); Michael F. Moyers, Colton, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 13/345,090

(22) Filed: Jan. 6, 2012

(65) Prior Publication Data
US 2012/0104276 A1    May 3, 2012

Related U.S. Application Data

(63) Continuation of application No. 12/758,645, filed on Apr. 12, 2010, now Pat. No. 8,093,569, which is a continuation of application No. 11/671,922, filed on Feb. 6, 2007, now Pat. No. 7,696,499, which is a continuation of application No. 10/917,022, filed on Aug. 12, 2004, now Pat. No. 7,173, 265.

(60) Provisional application No. 60/494,699, filed on Aug. 12, 2003, provisional application No. 60/579,095, filed on Jun. 10, 2004.

(51) Int. Cl.
*A61G 7/07* (2006.01)
(52) U.S. Cl.
USPC ..................... 5/601; 5/600; 5/621

(58) Field of Classification Search ............. 5/600–601, 5/621–623; 250/492.3; 378/208–209
See application file for complete search history.

(56) References Cited

U.S. PATENT DOCUMENTS

| 2,469,084 A | 5/1949 | Schenker |
| 2,675,564 A | 4/1954 | Hughes |

(Continued)

FOREIGN PATENT DOCUMENTS

| DE | 2513896 A1 | 10/1975 |
| DE | 2833800 A1 | 12/1979 |

(Continued)

OTHER PUBLICATIONS

Lawrence Berkeley Laboratory, et al., Dedicated Medical Ion Accelerator Design Study, Dec. 1977, PCTA008295-PCTA008455.

(Continued)

*Primary Examiner* — Fredrick Conley
(74) *Attorney, Agent, or Firm* — Knobbe Martens Olson & Bear LLP

(57) ABSTRACT

A radiation treatment system (100) for accurately delivering radiation to a targeted site within a cancer patient (108) that includes a modular patient support system and a patient positioner (114). The modular patient support system includes a modularly expandable patient pod (200) and at least one immobilization device, such as, for example, a rigid moldable foam cradle (350). The patient pod (200) includes a generally hemi-cylindrical support shell (212) that extends longitudinally between proximal edge (214) and distal edge (216), and transversely between two lateral edges (222, 224). In one embodiment, the lateral edges (222, 224) are tapered to minimize edge effects that result when radiation beams traverse the lateral edges (222, 224).

18 Claims, 11 Drawing Sheets

U.S. PATENT DOCUMENTS

| | | | |
|---|---|---|---|
| 3,397,411 A | 8/1968 | Rossi |
| 3,449,570 A | 6/1969 | Kok |
| 3,545,739 A | 12/1970 | D'Avignon |
| 3,556,455 A | 1/1971 | Storm |
| 3,604,931 A | 9/1971 | Kastner et al. |
| 3,640,787 A | 2/1972 | Heller |
| 3,689,949 A | 9/1972 | Weinstein et al. |
| 3,745,998 A | 7/1973 | Rose |
| 3,762,404 A | 10/1973 | Sakita |
| 3,778,049 A | 12/1973 | Viamonte, Jr. |
| 3,783,251 A | 1/1974 | Pavkovich |
| 3,848,132 A | 11/1974 | Foderaro |
| 3,851,644 A | 12/1974 | Slagle |
| 3,852,610 A | 12/1974 | McIntyre |
| 3,885,258 A | 5/1975 | Regan |
| 3,893,198 A | 7/1975 | Blair |
| 3,897,345 A | 7/1975 | Foster |
| 3,897,777 A | 8/1975 | Morrison |
| 3,901,588 A | 8/1975 | Longhenry |
| 3,905,054 A | 9/1975 | Windsor et al. |
| 3,942,012 A | 3/1976 | Boux |
| 3,947,686 A | 3/1976 | Cooper et al. |
| 3,986,697 A | 10/1976 | Amor, Jr. et al. |
| 4,034,224 A * | 7/1977 | Heavens et al. ................. 378/20 |
| 4,064,401 A | 12/1977 | Marden |
| 4,069,457 A | 1/1978 | Martin et al. |
| 4,095,114 A | 6/1978 | Taumann |
| 4,112,306 A | 9/1978 | Nunan |
| 4,146,793 A | 3/1979 | Bergstrom et al. |
| 4,190,772 A | 2/1980 | Dinwiddie et al. |
| 4,206,355 A | 6/1980 | Boux |
| 4,230,129 A | 10/1980 | LeVeen |
| 4,252,594 A | 2/1981 | Cooper |
| 4,256,112 A | 3/1981 | Kopf et al. |
| 4,262,204 A | 4/1981 | Mirabella |
| 4,269,512 A | 5/1981 | Nosler |
| 4,287,425 A | 9/1981 | Elliott, Jr. |
| 4,318,538 A | 3/1982 | Janssen |
| 4,327,046 A | 4/1982 | Davis et al. |
| 4,347,213 A | 8/1982 | Rogers, Jr. |
| 4,365,341 A | 12/1982 | Lam |
| 4,378,813 A | 4/1983 | Lovelace et al. |
| 4,392,239 A | 7/1983 | Wilkens |
| 4,400,820 A | 8/1983 | O'Dell et al. |
| 4,442,352 A | 4/1984 | Brahme |
| 4,450,122 A | 5/1984 | Gallina |
| 4,484,571 A * | 11/1984 | Velazquez ......................... 5/601 |
| 4,504,050 A | 3/1985 | Osborne |
| 4,552,508 A | 11/1985 | Reid |
| 4,578,757 A | 3/1986 | Stark |
| 4,591,341 A | 5/1986 | Andrews |
| 4,616,814 A | 10/1986 | Harwood-Nash et al. |
| 4,666,304 A | 5/1987 | Davies |
| 4,671,284 A | 6/1987 | Wilson et al. |
| 4,672,212 A | 6/1987 | Brahme |
| 4,682,818 A | 7/1987 | Morell |
| 4,688,780 A | 8/1987 | Hanz |
| 4,705,955 A | 11/1987 | Mileikowsky |
| 4,711,578 A | 12/1987 | Chaimowicz |
| 4,752,064 A | 6/1988 | Voss |
| 4,779,858 A | 10/1988 | Saussereau |
| 4,789,930 A | 12/1988 | Sones et al. |
| 4,796,613 A | 1/1989 | Heumann et al. |
| 4,812,658 A | 3/1989 | Koehler |
| 4,815,448 A | 3/1989 | Mills |
| 4,819,257 A | 4/1989 | Grasser et al. |
| 4,841,965 A | 6/1989 | Jacobs |
| 4,848,340 A | 7/1989 | Bille et al. |
| 4,870,287 A | 9/1989 | Cole et al. |
| 4,905,267 A | 2/1990 | Miller et al. |
| 4,917,344 A | 4/1990 | Prechter et al. |
| 4,926,457 A | 5/1990 | Poehner et al. |
| 4,979,519 A | 12/1990 | Chavarria et al. |
| 5,014,290 A | 5/1991 | Moore et al. |
| 5,017,789 A | 5/1991 | Young et al. |
| 5,037,374 A | 8/1991 | Carol |
| 5,039,057 A | 8/1991 | Prechter et al. |
| 5,039,867 A | 8/1991 | Nishihara et al. |
| 5,046,708 A | 9/1991 | Schaefer |
| 5,048,071 A | 9/1991 | Van Steenburg |
| 5,049,147 A | 9/1991 | Danon |
| 5,054,049 A * | 10/1991 | Manabe ........................ 378/208 |
| 5,079,426 A | 1/1992 | Antonuk et al. |
| 5,081,665 A | 1/1992 | Kostich |
| 5,090,047 A | 2/1992 | Angotti et al. |
| 5,094,241 A | 3/1992 | Allen |
| 5,107,839 A | 4/1992 | Houdek et al. |
| 5,117,445 A | 5/1992 | Seppi et al. |
| 5,117,829 A | 6/1992 | Miller et al. |
| 5,156,166 A | 10/1992 | Sebring |
| 5,168,514 A | 12/1992 | Horton, Jr. et al. |
| 5,207,688 A | 5/1993 | Carol |
| 5,230,623 A | 7/1993 | Guthrie et al. |
| 5,240,218 A | 8/1993 | Dye |
| 5,242,455 A | 9/1993 | Skeens et al. |
| 5,269,305 A | 12/1993 | Corol |
| 5,274,864 A | 1/1994 | Morgan |
| 5,276,927 A | 1/1994 | Day |
| 5,278,886 A | 1/1994 | Ohgushi et al. |
| 5,279,309 A | 1/1994 | Taylor et al. |
| 5,281,232 A | 1/1994 | Hamilton et al. |
| 5,287,576 A | 2/1994 | Fraser |
| 5,297,262 A | 3/1994 | Cox et al. |
| 5,343,048 A | 8/1994 | Pastyr |
| 5,361,765 A | 11/1994 | Herlihy et al. |
| 5,370,117 A | 12/1994 | McLaurin, Jr. |
| 5,370,118 A | 12/1994 | Vij et al. |
| 5,380,336 A | 1/1995 | Misko et al. |
| 5,382,914 A | 1/1995 | Hamm et al. |
| 5,388,580 A | 2/1995 | Sullivan et al. |
| 5,402,463 A | 3/1995 | Umetani et al. |
| 5,427,097 A | 6/1995 | Depp |
| 5,446,548 A | 8/1995 | Gerig et al. |
| 5,454,993 A | 10/1995 | Kostich |
| 5,464,411 A | 11/1995 | Schulte et al. |
| 5,485,502 A | 1/1996 | Hinton et al. |
| 5,485,833 A | 1/1996 | Dietz |
| 5,511,549 A | 4/1996 | Legg et al. |
| 5,531,229 A | 7/1996 | Dean et al. |
| 5,538,494 A | 7/1996 | Matsuda |
| 5,549,616 A | 8/1996 | Schulte |
| 5,566,681 A | 10/1996 | Manwaring et al. |
| 5,570,409 A | 10/1996 | Yamaguchi et al. |
| 5,577,707 A | 11/1996 | Brida |
| 5,588,430 A | 12/1996 | Bova et al. |
| 5,595,191 A | 1/1997 | Kirk |
| 5,596,619 A | 1/1997 | Carol |
| 5,602,892 A | 2/1997 | Llacer |
| 5,622,187 A | 4/1997 | Carol |
| 5,675,851 A | 10/1997 | Feathers |
| 5,676,673 A | 10/1997 | Ferre et al. |
| 5,727,554 A | 3/1998 | Kalend et al. |
| 5,745,545 A | 4/1998 | Hughes |
| 5,751,781 A | 5/1998 | Brown et al. |
| 5,771,512 A | 6/1998 | Kurakake et al. |
| 5,775,337 A | 7/1998 | Hauger et al. |
| 5,778,047 A | 7/1998 | Mansfield et al. |
| 5,792,147 A | 8/1998 | Evans et al. |
| 5,797,924 A | 8/1998 | Schulte et al. |
| 5,800,352 A | 9/1998 | Ferre et al. |
| 5,806,116 A | 9/1998 | Oliver et al. |
| 5,820,444 A | 10/1998 | McGaughey |
| 5,820,553 A | 10/1998 | Hughes |
| 5,823,192 A | 10/1998 | Kalend et al. |
| 5,825,845 A | 10/1998 | Blair et al. |
| 5,832,550 A | 11/1998 | Hauger et al. |
| 5,847,403 A | 12/1998 | Hughes et al. |
| 5,848,449 A | 12/1998 | Hauger et al. |
| 5,851,182 A | 12/1998 | Sahadevan |
| 5,865,832 A | 2/1999 | Knopp et al. |
| 5,895,926 A | 4/1999 | Britton et al. |
| 5,911,655 A | 6/1999 | Brenneisen |
| 5,947,981 A | 9/1999 | Cosman |
| 5,983,424 A | 11/1999 | Näslund |
| 6,003,174 A | 12/1999 | Kantrowitz et al. |
| 6,023,694 A | 2/2000 | Kouchi et al. |
| 6,026,392 A | 2/2000 | Kouchi et al. |

| Patent No. | Date | Inventor(s) |
|---|---|---|
| 6,085,227 A | 7/2000 | Edlund et al. |
| 6,094,760 A | 8/2000 | Nonaka et al. |
| 6,104,779 A | 8/2000 | Shepherd et al. |
| 6,118,848 A | 9/2000 | Reiffel |
| 6,144,875 A | 11/2000 | Schweikard et al. |
| 6,144,993 A | 11/2000 | Fukunaga et al. |
| 6,148,272 A | 11/2000 | Bergstrom et al. |
| 6,152,950 A | 11/2000 | Shealy et al. |
| 6,161,237 A | 12/2000 | Tang et al. |
| 6,178,430 B1 | 1/2001 | Cohen et al. |
| 6,180,942 B1 | 1/2001 | Tracy et al. |
| 6,182,060 B1 | 1/2001 | Hedgcock et al. |
| 6,195,578 B1 | 2/2001 | Distler et al. |
| 6,200,025 B1 | 3/2001 | Rich |
| 6,240,161 B1 | 5/2001 | Siochi |
| 6,244,745 B1 | 6/2001 | Mattern |
| 6,275,564 B1 | 8/2001 | Ein-Gal |
| 6,279,579 B1 | 8/2001 | Riaziat et al. |
| 6,282,739 B1 | 9/2001 | Livingston |
| 6,308,353 B1 | 10/2001 | Van Steenburg |
| 6,313,915 B1 | 11/2001 | Yanagisawa et al. |
| 6,316,776 B1 | 11/2001 | Hiramoto et al. |
| 6,325,758 B1 | 12/2001 | Carol et al. |
| 6,345,114 B1 | 2/2002 | Mackie et al. |
| 6,375,355 B1 | 4/2002 | Fortin |
| 6,376,846 B2 | 4/2002 | Livingston |
| 6,385,286 B1 | 5/2002 | Fitchard et al. |
| 6,405,072 B1 | 6/2002 | Cosman |
| 6,437,513 B1 | 8/2002 | Selzer et al. |
| 6,445,766 B1 | 9/2002 | Whitham |
| 6,446,286 B1 | 9/2002 | Karmalawy |
| 6,452,999 B1 | 9/2002 | Maida |
| 6,462,490 B1 | 10/2002 | Matsuda et al. |
| 6,462,553 B1 | 10/2002 | Badura |
| 6,466,813 B1 | 10/2002 | Shukla et al. |
| 6,473,490 B1 | 10/2002 | Siochi |
| 6,476,403 B1 | 11/2002 | Dolinskii et al. |
| 6,504,899 B2 | 1/2003 | Pugachev et al. |
| 6,505,245 B1 | 1/2003 | North et al. |
| 6,509,573 B1 | 1/2003 | Badura et al. |
| 6,565,577 B2 | 5/2003 | Cosman |
| 6,577,707 B2 | 6/2003 | Siochi |
| 6,597,005 B1 | 7/2003 | Badura et al. |
| 6,598,275 B1 | 7/2003 | Kolody et al. |
| 6,600,164 B1 | 7/2003 | Badura et al. |
| 6,614,038 B1 | 9/2003 | Brand et al. |
| 6,621,889 B1 | 9/2003 | Mostafavi |
| 6,639,234 B1 | 10/2003 | Badura et al. |
| 6,650,930 B2 | 11/2003 | Ding |
| 6,662,036 B2 | 12/2003 | Cosman |
| 6,665,555 B2 | 12/2003 | Henderson et al. |
| 6,670,618 B1 | 12/2003 | Hartmann et al. |
| 6,677,597 B1 | 1/2004 | Haberer et al. |
| 6,683,318 B1 | 1/2004 | Haberer et al. |
| 6,690,965 B1 | 2/2004 | Riaziat et al. |
| 6,693,283 B2 | 2/2004 | Eickhoff et al. |
| 6,698,045 B1 | 3/2004 | Coppens et al. |
| 6,704,957 B2 | 3/2004 | Rhodes |
| 6,710,362 B2 | 3/2004 | Kraft et al. |
| 6,725,078 B2 | 4/2004 | Bucholz et al. |
| 6,730,921 B2 | 5/2004 | Kraft |
| 6,731,970 B2 | 5/2004 | Schlossbauer et al. |
| 6,736,831 B1 | 5/2004 | Hartmann et al. |
| 6,745,072 B1 | 6/2004 | Badura et al. |
| 6,754,299 B2 | 6/2004 | Patch |
| 6,757,355 B1 | 6/2004 | Siochi |
| 6,769,806 B2 | 8/2004 | Moyers |
| 6,774,383 B2 | 8/2004 | Norimine et al. |
| 6,777,700 B2 | 8/2004 | Yanagisawa et al. |
| 6,780,149 B1 | 8/2004 | Schulte |
| 6,792,078 B2 | 9/2004 | Kato et al. |
| 6,795,523 B2 | 9/2004 | Steinberg |
| 6,799,068 B1 | 9/2004 | Hartmann et al. |
| 6,803,591 B2 | 10/2004 | Muramatsu et al. |
| 6,804,548 B2 | 10/2004 | Takahashi et al. |
| 6,809,325 B2 | 10/2004 | Dahl et al. |
| 6,810,107 B2 | 10/2004 | Steinberg |
| 6,813,788 B2 | 11/2004 | Dinkler et al. |
| 6,814,694 B1 | 11/2004 | Pedroni |
| 6,822,244 B2 | 11/2004 | Beloussov et al. |
| 6,839,404 B2 | 1/2005 | Clark et al. |
| 6,842,502 B2 | 1/2005 | Jaffray et al. |
| 6,855,942 B2 | 2/2005 | Bechthold et al. |
| 6,859,741 B2 | 2/2005 | Haberer et al. |
| 6,865,411 B2 | 3/2005 | Erbel et al. |
| 6,873,123 B2 | 3/2005 | Marchand et al. |
| 6,891,177 B1 | 5/2005 | Kraft et al. |
| 6,895,617 B2 | 5/2005 | Zacharopoulos et al. |
| 6,904,630 B2 | 6/2005 | Al-Kassim et al. |
| 6,907,629 B2 | 6/2005 | Longton et al. |
| 6,968,036 B2 | 11/2005 | Carlsson et al. |
| 6,977,987 B2 | 12/2005 | Yamashita et al. |
| 7,008,105 B2 | 3/2006 | Amann et al. |
| 7,011,447 B2 | 3/2006 | Moyers |
| 7,063,461 B2 | 6/2006 | Coppens et al. |
| 7,073,508 B2 | 7/2006 | Moyers |
| 7,076,821 B2 | 7/2006 | de Mooy |
| 7,084,410 B2 | 8/2006 | Beloussov et al. |
| 7,091,478 B2 | 8/2006 | Haberer |
| 7,120,223 B2 | 10/2006 | Nafstadius |
| 7,142,634 B2 | 11/2006 | Engler et al. |
| 7,154,108 B2 | 12/2006 | Tadokoro et al. |
| 7,154,991 B2 | 12/2006 | Earnst et al. |
| 7,173,264 B2 | 2/2007 | Moriyama et al. |
| 7,173,265 B2 | 2/2007 | Miller et al. |
| 7,188,999 B2 | 3/2007 | Mihara et al. |
| 7,199,382 B2 | 4/2007 | Rigney et al. |
| 7,207,715 B2 | 4/2007 | Yue |
| 7,212,608 B2 | 5/2007 | Nagamine et al. |
| 7,280,633 B2 | 10/2007 | Cheng et al. |
| 7,301,162 B2 | 11/2007 | Matsuda et al. |
| 7,331,713 B2 | 2/2008 | Moyers |
| 7,348,579 B2 | 3/2008 | Pedroni |
| 7,368,740 B2 | 5/2008 | Beloussov et al. |
| 7,372,053 B2 | 5/2008 | Yamashita et al. |
| 7,398,309 B2 | 7/2008 | Baumann et al. |
| 7,446,328 B2 | 11/2008 | Rigney et al. |
| 7,486,983 B2 | 2/2009 | Ghelmansarai et al. |
| 7,497,689 B2 | 3/2009 | Sommer |
| 7,560,717 B2 | 7/2009 | Matsuda et al. |
| 7,582,886 B2 | 9/2009 | Trbojevic |
| 7,587,024 B2 | 9/2009 | Grozinger |
| 7,589,334 B2 | 9/2009 | Hiramoto et al. |
| 7,603,164 B2 | 10/2009 | Uematsu |
| 7,659,521 B2 | 2/2010 | Pedroni |
| 7,696,499 B2 | 4/2010 | Miller et al. |
| 7,796,730 B2 | 9/2010 | Marash et al. |
| 7,949,096 B2 | 5/2011 | Cheng et al. |
| 7,984,715 B2 | 7/2011 | Moyers |
| 8,093,569 B2 | 1/2012 | Miller et al. |
| 2002/0027969 A1 | 3/2002 | Maida |
| 2002/0032378 A1 | 3/2002 | Henderson et al. |
| 2002/0051513 A1 | 5/2002 | Pugachev et al. |
| 2002/0065461 A1 | 5/2002 | Cosman |
| 2002/0077545 A1 | 6/2002 | Takahashi et al. |
| 2002/0095730 A1 | 7/2002 | Al-Kassim et al. |
| 2002/0120986 A1 | 9/2002 | Erbel et al. |
| 2002/0188194 A1 | 12/2002 | Cosman |
| 2002/0193685 A1 | 12/2002 | Mate et al. |
| 2003/0007601 A1 | 1/2003 | Jaffray et al. |
| 2003/0031301 A1 | 2/2003 | Longton et al. |
| 2003/0086527 A1 | 5/2003 | Speiser et al. |
| 2003/0095625 A1 | 5/2003 | Steinberg |
| 2003/0164459 A1 | 9/2003 | Schardt et al. |
| 2003/0183779 A1 | 10/2003 | Norimine et al. |
| 2004/0013414 A1 | 1/2004 | Karger et al. |
| 2004/0028188 A1 | 2/2004 | Amann et al. |
| 2004/0034438 A1 | 2/2004 | Uematsu |
| 2004/0034932 A1 | 2/2004 | Zacharopoulos et al. |
| 2004/0042583 A1 | 3/2004 | Wackerle et al. |
| 2004/0082856 A1 | 4/2004 | Marmarelis |
| 2004/0098445 A1 | 5/2004 | Baumann et al. |
| 2004/0123388 A1 | 7/2004 | Coppens et al. |
| 2004/0155206 A1 | 8/2004 | Marchand et al. |
| 2004/0158145 A1 | 8/2004 | Ghelmansarai et al. |
| 2004/0164254 A1 | 8/2004 | Beloussov et al. |
| 2004/0174958 A1 | 9/2004 | Moriyama et al. |
| 2004/0184579 A1 | 9/2004 | Mihara et al. |

| | | | |
|---|---|---|---|
| 2004/0184583 A1 | 9/2004 | Nagamine et al. | |
| 2005/0054910 A1 | 3/2005 | Tremblay et al. | |
| 2005/0072940 A1 | 4/2005 | Beloussov et al. | |
| 2005/0116175 A1 | 6/2005 | Haberer | |
| 2005/0161618 A1 | 7/2005 | Pedroni | |
| 2005/0281374 A1 | 12/2005 | Cheng et al. | |
| 2006/0002511 A1 | 1/2006 | Miller et al. | |
| 2006/0017022 A1 | 1/2006 | Rigney et al. | |
| 2006/0183960 A1 | 8/2006 | Sioshansi et al. | |
| 2007/0018120 A1 | 1/2007 | Beloussov et al. | |
| 2007/0018121 A1 | 1/2007 | Leyman et al. | |
| 2007/0025524 A1 | 2/2007 | Yue | |
| 2007/0031337 A1 | 2/2007 | Schulte | |
| 2007/0093100 A1 | 4/2007 | Sommer | |
| 2007/0108922 A1 | 5/2007 | Amaldi | |
| 2007/0158592 A1 | 7/2007 | Hiramoto et al. | |
| 2007/0164230 A1 | 7/2007 | Rigney et al. | |
| 2007/0262269 A1 | 11/2007 | Trbojevic | |
| 2008/0005643 A1 | 1/2008 | Park et al. | |
| 2008/0031414 A1 | 2/2008 | Coppens | |
| 2008/0042076 A1 | 2/2008 | Miller et al. | |
| 2008/0056434 A1 | 3/2008 | Grozinger et al. | |
| 2008/0187097 A1 | 8/2008 | Cheng et al. | |
| 2008/0189859 A1 | 8/2008 | Sloan et al. | |
| 2008/0191142 A1 | 8/2008 | Pedroni | |
| 2008/0192892 A1 | 8/2008 | Dilmanian et al. | |
| 2008/0237494 A1 | 10/2008 | Beloussov et al. | |
| 2008/0292053 A1 | 11/2008 | Marash et al. | |
| 2008/0317216 A1 | 12/2008 | Lifshitz et al. | |
| 2009/0067577 A1 | 3/2009 | Rigney et al. | |
| 2009/0154645 A1 | 6/2009 | Lifshitz et al. | |
| 2009/0202045 A1 | 8/2009 | Guertin et al. | |
| 2009/0217456 A1 | 9/2009 | Lempen et al. | |

FOREIGN PATENT DOCUMENTS

| | | |
|---|---|---|
| DE | 3643893 | 6/1988 |
| DE | 4418216 A1 | 11/1995 |
| DE | 19612091 A1 | 3/1997 |
| DE | 102 00 534 | 7/2003 |
| DE | 102005034912 | 2/2007 |
| EP | 019136 | 11/1980 |
| EP | 0247449 A1 | 12/1987 |
| EP | 0283082 A1 | 9/1988 |
| EP | 0465590 A1 | 1/1992 |
| EP | 0480035 A1 | 4/1992 |
| EP | 0809525 A1 | 12/1997 |
| EP | 0986070 A1 | 3/2000 |
| EP | 0986071 A1 | 3/2000 |
| EP | 1064881 | 1/2001 |
| EP | 1064881 A1 | 1/2001 |
| EP | 1454653 A1 | 9/2004 |
| EP | 1584353 A1 | 10/2005 |
| EP | 1585578 | 10/2005 |
| EP | 1709994 A1 | 10/2006 |
| EP | 1792595 A1 | 6/2007 |
| EP | 1795229 A1 | 6/2007 |
| EP | 1900392 A1 | 3/2008 |
| EP | 1935453 A2 | 6/2008 |
| EP | 2108402 | 10/2009 |
| FR | 2701391 A1 | 8/1994 |
| GB | 870225 A | 6/1961 |
| GB | 1362678 A | 8/1974 |
| GB | 2213066 A | 8/1989 |
| GB | 2254691 A | 10/1992 |
| JP | 58-98902 | 7/1983 |
| JP | 58-131816 | 9/1983 |
| JP | S58-171615 | 10/1983 |
| JP | 63-206261 | 8/1988 |
| JP | 03-94736 | 4/1991 |
| JP | 04-129572 | 4/1992 |
| JP | 04217150 A | 8/1992 |
| JP | 04-339282 | 11/1992 |
| JP | 61194400 A | 4/1994 |
| JP | 6-225871 | 8/1994 |
| JP | 07-163670 | 6/1995 |
| JP | 07-204184 | 8/1995 |
| JP | 8-501970 | 3/1996 |
| JP | 08-266650 | 10/1996 |
| JP | 2001-259060 | 9/2001 |
| JP | 2002536119 | 10/2002 |
| JP | 2003527763 T | 9/2003 |
| JP | 11-099491 | 4/2009 |
| NL | 7309246 A | 10/1974 |
| WO | WO 88/01848 A1 | 3/1988 |
| WO | WO 90/11721 A1 | 10/1990 |
| WO | WO 90/11723 A1 | 10/1990 |
| WO | WO 9625200 | 8/1996 |
| WO | WO 9852646 | 11/1998 |
| WO | WO 99/10137 A1 | 3/1999 |
| WO | WO 00/16175 A1 | 3/2000 |
| WO | WO 00/59575 A1 | 10/2000 |
| WO | WO 01/00276 A1 | 1/2001 |
| WO | WO 01/89625 A1 | 11/2001 |
| WO | WO 02/63638 A1 | 2/2002 |
| WO | WO 02/23121 | 3/2002 |
| WO | WO 0245793 | 6/2002 |
| WO | WO 02/100485 A1 | 12/2002 |
| WO | WO 03/039212 A1 | 5/2003 |
| WO | WO 03/053520 A1 | 7/2003 |
| WO | WO 03/076016 A1 | 9/2003 |
| WO | WO 2004/026401 A1 | 4/2004 |
| WO | WO 2004/032781 A1 | 4/2004 |
| WO | WO 2004060486 | 7/2004 |
| WO | WO 2005/018734 A2 | 3/2005 |
| WO | WO 2005/018735 A2 | 3/2005 |
| WO | WO 2005/037167 A2 | 4/2005 |
| WO | WO 2005/102453 A1 | 11/2005 |
| WO | WO 2006/060886 A1 | 6/2006 |
| WO | WO 2006/076545 A2 | 7/2006 |
| WO | WO 2006/094533 A1 | 9/2006 |
| WO | WO 2007012646 | 2/2007 |
| WO | WO 2007016022 | 2/2007 |
| WO | WO 2007/054140 A1 | 5/2007 |
| WO | WO 2007/061426 A2 | 5/2007 |
| WO | WO 2007/062788 A1 | 6/2007 |
| WO | WO 2007/068066 A2 | 6/2007 |
| WO | WO 2007/127970 A2 | 11/2007 |
| WO | WO 2008003526 | 1/2008 |
| WO | WO 2008/051358 A1 | 5/2008 |
| WO | WO 2008/064271 A2 | 5/2008 |
| WO | WO 2008/081480 A1 | 7/2008 |
| WO | WO 2008/142695 A1 | 11/2008 |

OTHER PUBLICATIONS

Fermi National Accelerator Laboratory, Design of a Proton Therapy Synchrotron, Jun. 1986, LL467-LL574.

Fermilab, Proceedings of a Medical Workshop on Accelerators for Charged-Particle Beam Therapy, Jan. 1989, LL33170-LL33313.

Brianlab Radiotherapy Solutions, Product Overview, Copyright 2004, BrianLAB AG.

Fermi National Accelerator Laboratory, Proton Therapy Facility: Engineering Design Report, Feb. 1987, LL45441-LL45570.

Brobeck Corporation, Proton Therapy System, Nov. 1985, LL54413-LL54459.

www.Bioinstruments.Net/CP-100, CPI Product Overview, CP-100 Robot Patient Positioner, 2007.

Matsu'Ura, Jun, "Systems for Overall Control and Beam Transport of the HIMAC," Mitsubishi Electric Advance, Mitsubishi Electric Corporation, Tokyo, JP, vol. 72, Sep. 1995, pp. 5-7.

* cited by examiner

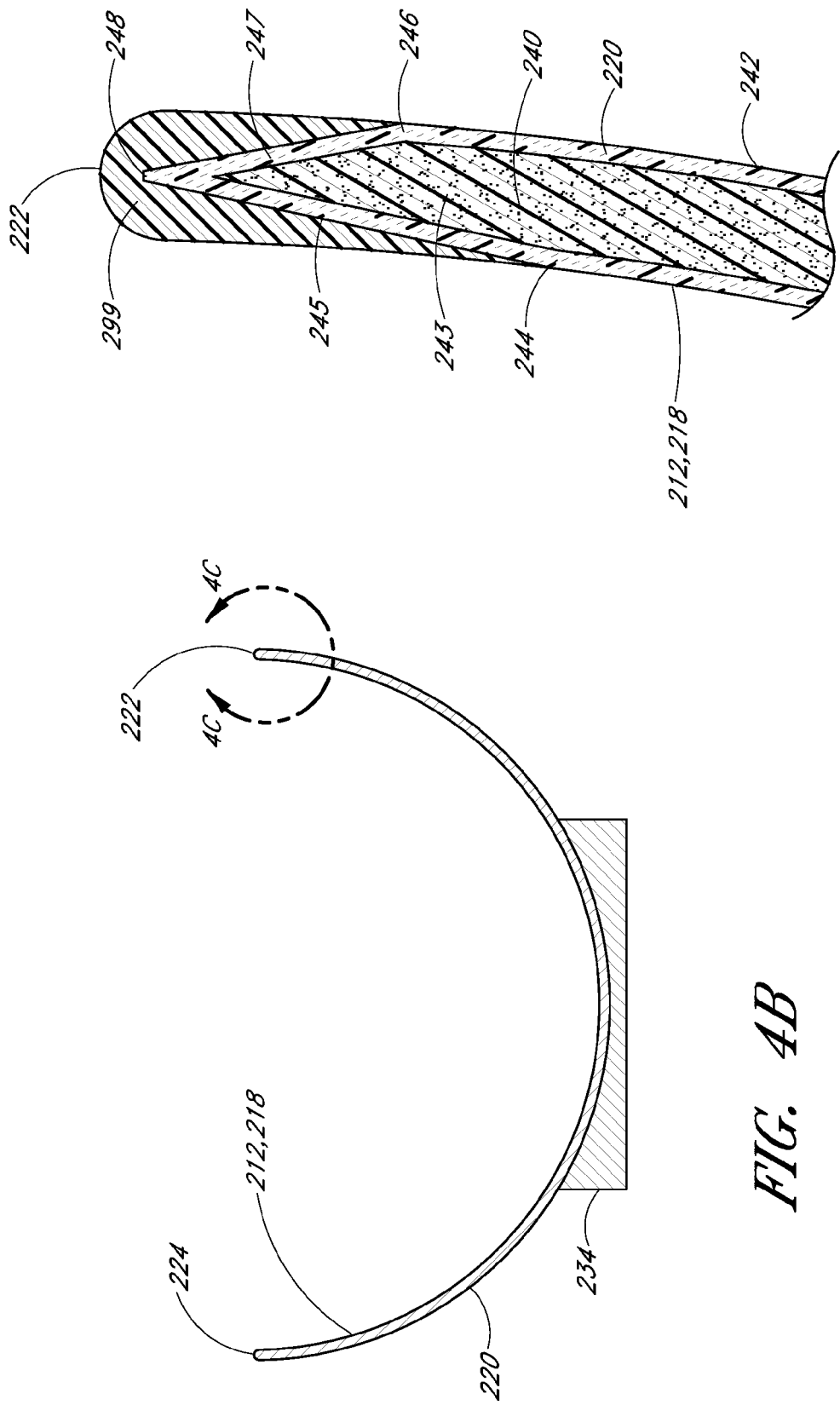

US 8,418,288 B2

MODULAR PATIENT SUPPORT SYSTEM

RELATED APPLICATIONS

This application is a continuation of U.S. application Ser. No. 12/758,645, filed Apr. 12, 2010, which is a continuation of U.S. application Ser. No. 11/671,922, filed Feb. 6, 2007, now U.S. Pat. No. 7,696,499, which is a continuation of U.S. application Ser. No. 10/917,022, filed Aug. 12, 2004, now U.S. Pat. No. 7,173,265, which claims priority to U.S. Provisional Application No. 60/494,699, filed Aug. 12, 2003, and to U.S. Provisional Application No. 60/579,095, filed Jun. 10, 2004. The disclosures of all of the above-referenced prior applications, publications, and patents are considered part of the disclosure of this application, and are incorporated by reference herein in their entirety.

GOVERNMENT SUPPORT

This invention was made with United States Government support under grants DAMD17-99-1-9477 and DAMD17-02-1-0205 awarded by the Department of Defense. The Government has certain rights in the invention.

BACKGROUND OF THE INVENTION

1. Field of the Invention

The present invention relates to radiation beam therapy systems, and more particularly to a radiation treatment system with a patient positioner. The present invention relates to radiation beam therapy systems, and more particularly to a modular patient support system. The present invention relates to radiation beam therapy systems, and more particularly to a patient pod with tapered edge configurations that reduce edge effects associated with abrupt changes in the water equivalency in the radiation beam path.

2. Description of the Related Art

Radiation therapy systems are known and used to provide treatment to patients suffering a wide variety of conditions. Radiation therapy is typically used to kill or inhibit the growth of undesired tissue, such as cancerous tissue. A determined quantity of high-energy electromagnetic radiation and/or high-energy particles are directed into the undesired tissue with the goal of damaging the undesired tissue while reducing unintentional damage to desired or healthy tissue through which the radiation passes on its path to the undesired tissue.

Proton therapy has emerged as a particularly efficacious treatment for a variety of conditions. In proton therapy, positively charged proton subatomic particles are accelerated, collimated into a tightly focused beam, and directed towards a designated target region within the patient. Protons exhibit less lateral dispersion upon impact with patient tissue than electromagnetic radiation or low mass electron charged particles and can thus be more precisely aimed and delivered along a beam axis. Also, upon impact with patient tissue, protons exhibit a characteristic Bragg peak wherein a significant portion of the kinetic energy of the accelerated mass is deposited within a relatively narrow penetration depth within the patient. This offers the significant advantage of reducing delivery of energy from the accelerated proton particles to healthy tissue interposed between the target region and the delivery nozzle of a proton therapy machine as well as to "downrange" tissue lying beyond the designated target region. Depending on the indications for a particular patient and their condition, delivery of the therapeutic proton beam may preferably take place from a plurality of directions in multiple treatment fractions to maintain a total dose delivered to the target region while reducing collateral exposure of interposed desired/healthy tissue.

U.S. Pat. No. 4,870,287, issued Sep. 26, 1989, assigned to the Loma Linda University Medical Center, titled MULTI-STATION PROTON BEAM THERAPY SYSTEM, describes and illustrates a radiation beam therapy system. The system described therein includes several different treatment stations, each including a gantry for supporting and rotating a radiation beam transport and delivery system on an axis of rotation around a stationary patient to deliver a treatment beam to a predetermined target isocenter within the patient from several different angles.

With many radiation treatment systems and protocols, a unique treatment plan is first developed for each cancer patient. For example, in the development of a treatment plan, such as, for example, proton radiation treatment, the patient is generally positioned on a support table or support structure and the internal anatomy of the patient's body scanned with an imaging technique, such as, for example, computed tomography (CT Scan). Images produced by the imaging device are analyzed to precisely locate the cancer sites defining the targets for the radiation beams. In many cases, physicians develop a radiation treatment plan calling for a number of different patient treatment sessions with radiation beams of different magnitudes, durations and angles of direction.

Given the high number of cancer patients who could benefit from radiation treatment and the relatively few number of sophisticated radiation (e.g., proton) treatment facilities and systems available in the world, there is a need for radiation treatment providers to achieve greater patient throughput at their existing facilities. As such, there is a need for patient support and positioning systems that utilize automated or robotic patient positioning devices, and thereby provide radiation treatment providers with the ability to achieve increased patient throughput.

For each treatment session, it is important that the patient be supported in the exact same position as during the preliminary imaging or scanning session utilized in the development of the treatment plan (i.e., the original position). Accordingly, there is a need for a patient positioning and repositioning support system for fixedly securing a patient in an original position during radiation treatment and for repositioning the patient in the same original position during any subsequent radiation treatment sessions. For certain applications that involve irradiating different portions of a patient's anatomy from several different angles, it is desirable for the patient positioning and repositioning support to fixedly secure the patient.

The radiation treatment protocol for any given patient can depend on a number of factors, including, for example: the size and physical characteristics of the patient; the type, size, and location of the tumor(s) being irradiated; and the aggressiveness of the treatment protocol. As such, there is a need for a modular patient support system that can be easily adjusted to accommodate a large number of treatment protocols.

For certain treatment protocols it is necessary to direct the radiation beam at angles that traverse at least one lateral edge of the patient pod. Accordingly, there is a need for pod edge configuration that reduces discontinuities in the strength or intensity of radiation beams that pass through or near a pod lateral edge.

SUMMARY OF THE INVENTION

In accordance with one embodiment described herein, there is provided a radiation treatment system for delivering prescribed doses of radiation to a targeted site within a cancer patient and for increasing patient throughput levels. The treatment system includes: a patient treatment station; a gantry, a radiation beam source; a nozzle; a modular patient support system; a patient positioner; and a control system.

In one embodiment, the radiation beam source includes a source of protons and an accelerator for accelerating protons as a beam.

In accordance with one embodiment described herein, there is provided a modular patient support system for efficiently securing a cancer patient in a fixed position during radiation treatment. The support system includes a modular patient pod.

In accordance with one embodiment described herein, there is provided a modular patient pod for providing cantilevered support of a cancer patient undergoing radiation treatment. The pod includes: a longitudinally-extending support shell; a proximal extension track; a distal extension track; and a positioner-pod connector.

In one embodiment, the support shell is made from a treat-through material, such as, for example, carbon fiber.

In one embodiment, a distal pod attachment is engaged with the distal extension track. In another embodiment, a proximal pod attachment is engaged with the proximal extension track.

In accordance with one embodiment described herein, there is provided a modular patient pod that is configured to reduce any edge effects. The pod includes a support shell having a first lateral edge and a second lateral edge.

In one embodiment, the first lateral edge includes a first tapered edge and a first rail made from a first low-density material, such as, for example, epoxy with microspheres. In another embodiment, the second lateral edge includes a second tapered edge and a second rail made from a second low-density material.

BRIEF DESCRIPTION OF THE DRAWINGS

FIG. 4B is a transverse cross-sectional view of the patient pod of FIG. 4A.

FIG. 4C is a close-up cross-sectional view of the pod shell lateral edge of FIG. 4B.

DETAILED DESCRIPTION OF THE PREFERRED EMBODIMENT

A. Radiation Treatment System with Robotic Patient Positioner

In accordance with one embodiment described herein, there is provided a radiation treatment system with a patient positioner.

Figure 1:
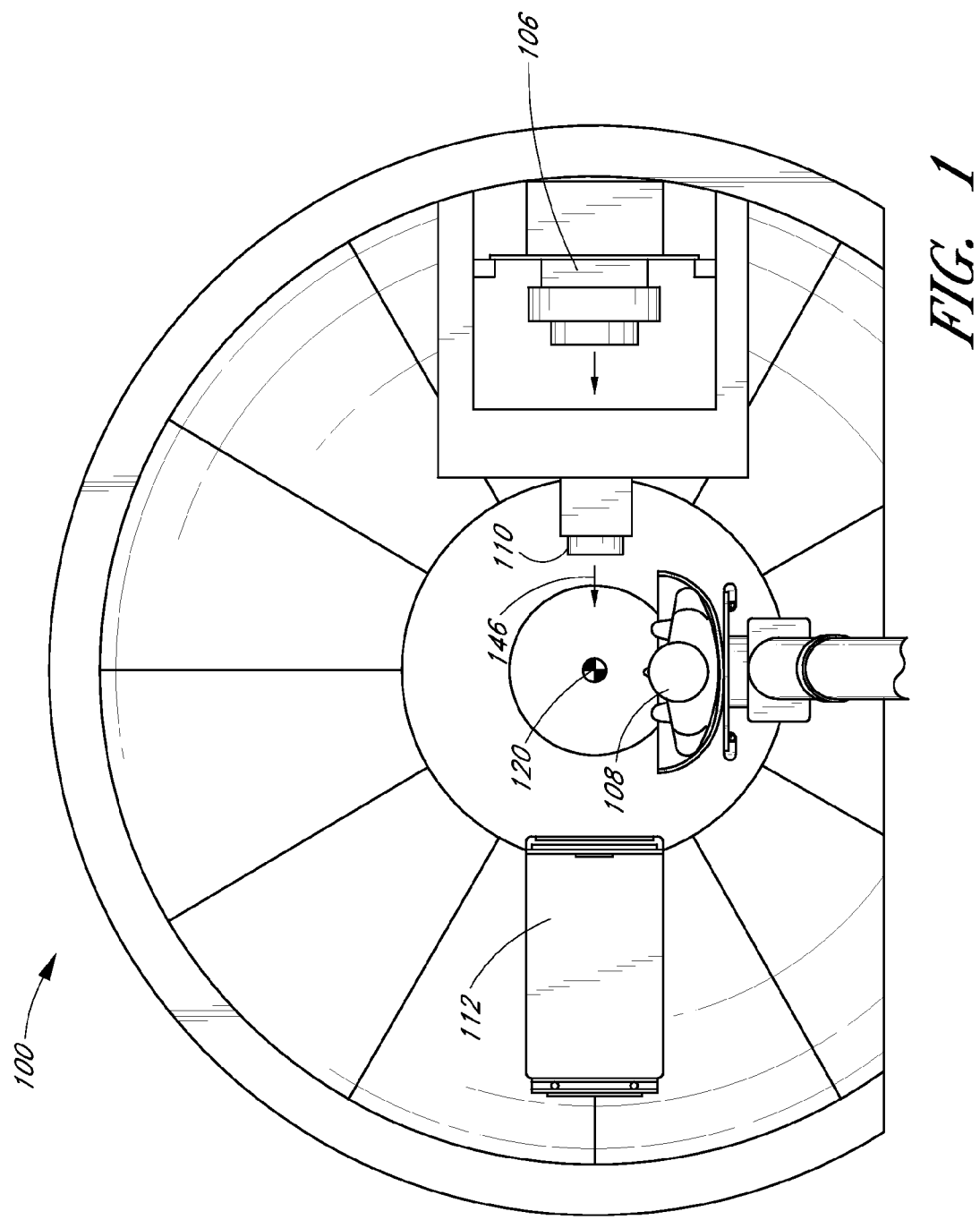
FIG. 1 is a schematic diagram of one embodiment of a radiation therapy system with a robotic patient positioning system.

Reference will now be made to the drawings wherein like reference designators refer to like parts throughout. FIG. 1 illustrates schematically one embodiment of a radiation therapy system 100. The radiation therapy system 100 is designed to deliver therapeutic radiation doses to a target region within a cancer patient 108 for treatment of malignant or other conditions from one or more angles or orientations with respect to the patient.

In one embodiment, the radiation therapy system 100 is designed to deliver therapeutic doses of proton beams to a target area within the patient. Additional details on the structure and operation of such a system 100 can be found in U.S. Pat. No. 4,870,287, titled MULTI-STATION PROTON BEAM THERAPY SYSTEM, which is incorporated herein in its entirety by reference. In another embodiment, the system 100 is designed to deliver any other clinically suitable form of radiation known in the art, such as, for example, x-rays, gamma rays, hadrons, neutrons, etc.

The radiation therapy system 100 typically includes a patient treatment station and a gantry 102 which includes a generally hemispherical or frustoconical support frame for attachment and support of other components of the radiation therapy system 100. Additional details on the structure and operation of the gantry 102 can be found in U.S. Pat. No. 4,917,344 and U.S. Pat. No. 5,039,057, both titled ROLLER-SUPPORTED, MODULAR, ISOCENTRIC GENTRY AND METHOD OF ASSEMBLY, both of which are incorporated herein in their entirety by reference.

With continued reference to FIG. 1, in one embodiment, the system 100 also comprises a nozzle 110 which is attached and supported by the gantry 102 such that the nozzle 110 may revolve relatively precisely about a gantry isocenter 120. The system 100 also comprises a radiation source 106 delivering a therapeutic beam, such as a beam of accelerated protons which pass through and are shaped by an aperture 110 positioned on the distal end of the nozzle 110. The beam path is represented by numeral 146. The aperture is preferably configured for the patient's particular prescription of therapeutic radiation therapy.

With continued reference to FIG. 1, the system 100 also comprises one or more imagers 112 which, in this embodiment, is retractable with respect to the gantry 102 between an extended position and a retracted position. Here, the imager 112 is shown in the extended position. In one embodiment, the imager 112 comprises a solid-state amorphous silicon x-ray imager which can develop image information such as from incident x-ray radiation that has passed through a patient's body. The system 100 also comprises an x-ray source 130 which selectively emits appropriate x-ray radiation which passes through interposed patient tissue so as to generate a radiographic image of the interposed materials via the imager 112. The retractable aspect of the imager 112 provides the advantage of withdrawing the imager screen from the beam path of the radiation source 106 when the imager 112 is not needed thereby providing additional clearance within the gantry 102 enclosure as well as placing the imager 112 out of the path of potentially harmful emissions from the radiation source 102 thereby reducing the need for shielding to be provided to the imager 112. In this embodiment, the imagers and radiation sources 130 are arranged orthogonally to provide a radiographic images of the patient from two directions.

The system 100 also comprises a patient positioner 114 and a patient pod 200 which is attached to positioner-pod connector 234 at the distal, working end 116 of the patient positioner 114. The patient positioner 114 is adapted to, upon receipt of appropriate movement commands, position the patient pod 200 in multiple translational and rotational axes and preferably is capable of positioning the patient pod 200 in three orthogonal translational (i.e., the longitudinal, vertical, and lateral) axes as well as three orthogonal rotational (i.e., pitch, roll, and yaw) axes so as to provide a full six degrees freedom of motion to placement of the patient pod 200.

It will be understood that the patient can be positioned in any number of ways, including, but not limited to, automatic, semi-automatic (e.g., with a hand pendent), manual controlled with direct interface to the positioner controller, or full manual (e.g., releasing a brake and moving each device axis with a hand crank).

Figure 2:
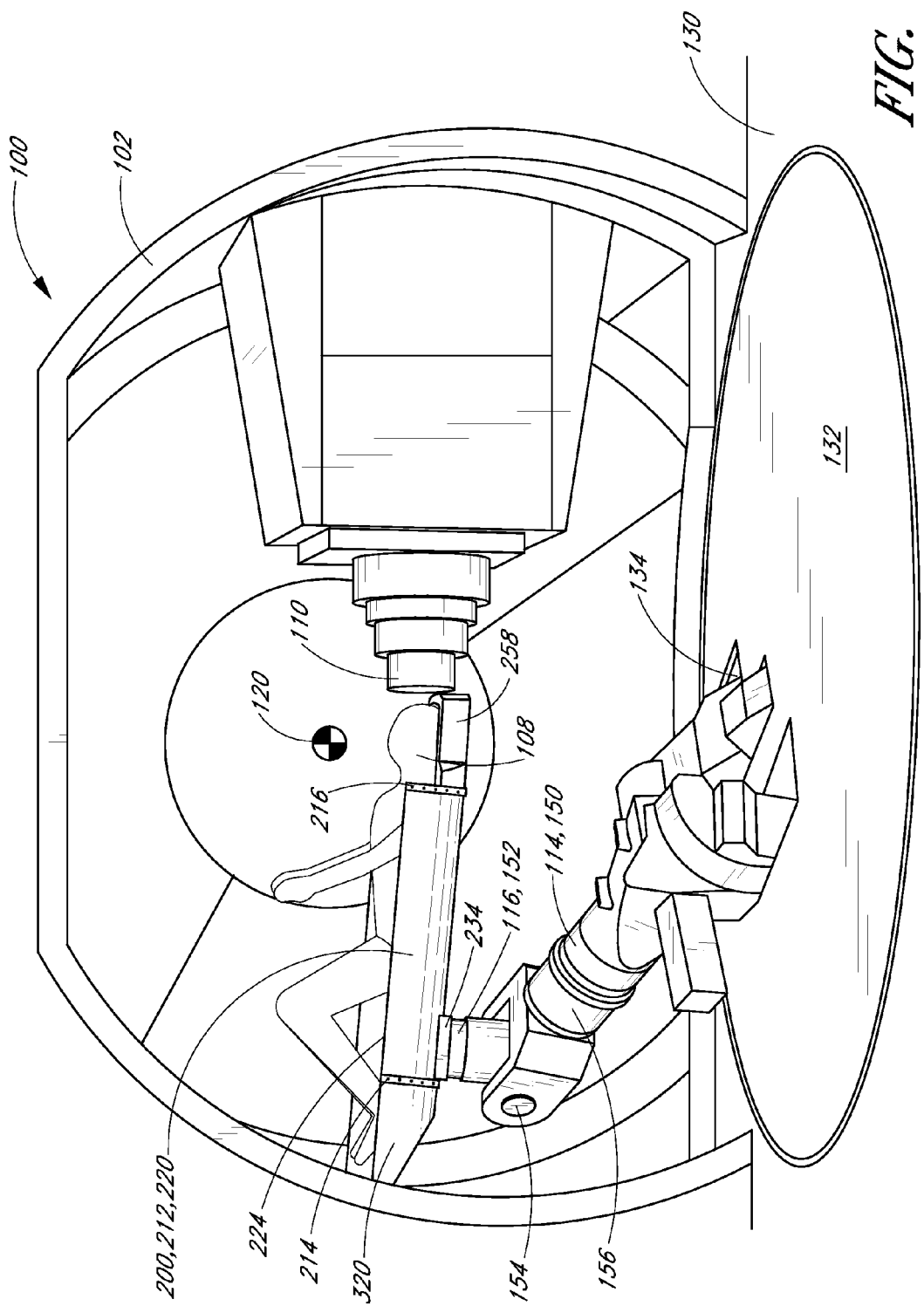
FIG. 2 is a schematic diagram of another embodiment of a radiation therapy system with a robotic patient positioning system.
Figure 3:
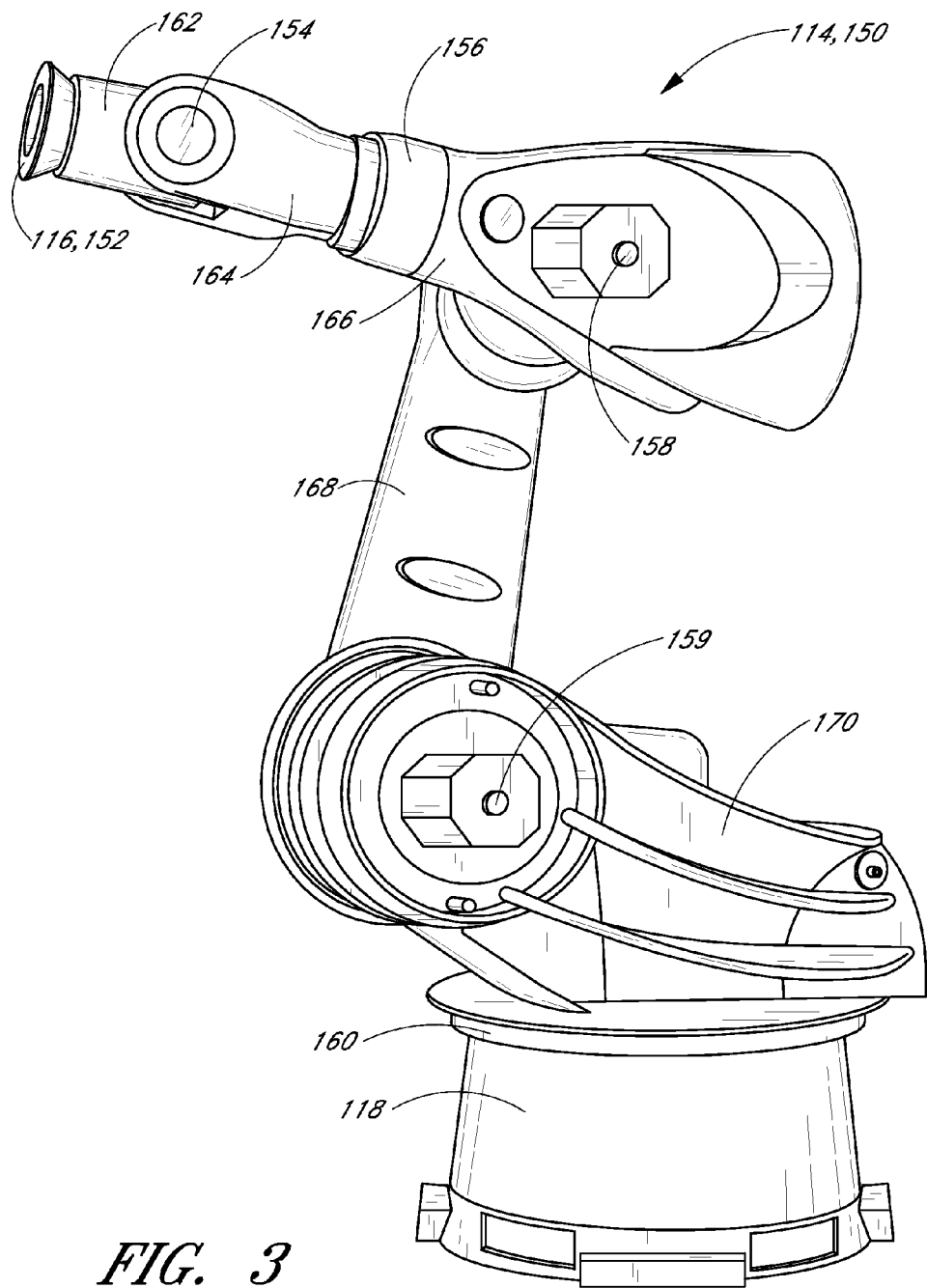
FIG. 3 is a side isometric view of one embodiment of a robotic patient positioner.

With reference to FIGS. 2 and 3, in one embodiment, the patient positioner 114 comprises a robotic arm 150, such as, for example, a KUKA KR500-L420 robot. In one embodiment, the KUKA KR500-L420 robot is safely mounted on a pedestal located in a pit beneath a rotating platform 132, and extends up through a cut-out 134 in the platform 132. The platform 132 is generally flush with the treatment area floor 130. The robotic arm 150 can typically move in six degrees of freedom and has the reach necessary to achieve all possible treatment positions in the gantry 102. The robotic arm 150 extends between a base 118 and a distal, working end 116.

A swivel joint 152 at the distal end 116 of the robotic arm 150 is capable of rotating any devices connected to its distal end in a clockwise or counterclockwise manner. The swivel joint 152 typically interfaces with a positioner-pod connector 234, which in turn connects with a patient pod 200. Robotic arm segment 162 and any distally located arm components are capable of being rotated about swivel joint 154. Robotic arm segment 164 and any distally located arm components are capable of being rotated about swivel joint 156. Robotic arm segment 166 and any distally located arm components are capable of being rotated about swivel joint 158. Robotic arm segment 168 and any distally located arm components are capable of being rotated about swivel joint 159. Robotic arm segment 170 and any distally located arm components are capable of being rotated about swivel joint 160.

With reference to FIG. 2, in one embodiment, the radiation therapy system 100 comprises an imager 112 that is in a retracted position or configuration, and thus hidden from view. The patient positioner 114 is mounted on a pedestal located in a pit beneath a rotating platform 132. The platform 132 is generally flush with the treatment area floor 130 and generally follows the rotational motion of the positioner 114 at the base 118 of the positioner 114. The robotic arm 150 of the positioner 114 extends up through a cut-out 134 in the platform 132. In one embodiment, shown in FIGS. 2 and 3, the platform 132 rotates in the clockwise or counterclockwise direction and follows the rotational motion about swivel joint 160.

Figure 5:
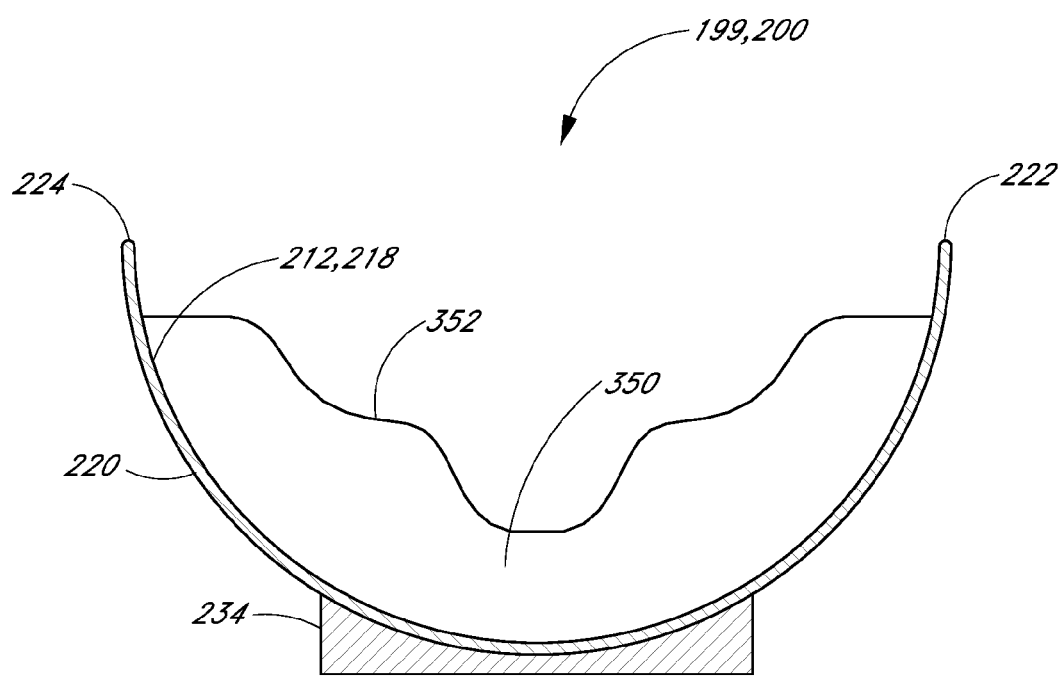
FIG. 5 is a transverse cross-sectional view of one embodiment of a modular patient support system.

With reference to FIGS. 2 and 5, in one embodiment, the radiation treatment system 100 comprises a modular patient support system 199 which interfaces with the patient positioner 114. More specifically, the distal end 116 of the robotic arm 150 interfaces with a patient pod 200, described in further detail below.

The system 100 is under regulation and operator control through a control system that is generally patterned after the system used for the Loma Linda University Medical Center 200 MeV synchrotron facility. The control system provides an operator controllable system for controlling the rotational position of the gantry 102, as well as the translational and rotational position of the patient positioner 114. The control system provides timing pulses to the entire system 100.

In one embodiment, the control system comprises multiple distributed microprocessor-based systems networked together and to a workstation computer using a Local Area Network (LAN) Standard. The LAN is an Ethernet based protocol. The workstation performs the centralized coordination of beam requests from the treatment stations in the therapy system as well as programmed beam-energy control.

Additional details on the structure and operation of the radiation therapy systems can be found in commonly assigned applications—namely, U.S. Pat. No. 7,280,633, issued on Oct. 9, 2007, titled PATH PLANNING AND COLLISION AVOIDANCE FOR MOVEMENT OF INSTRUMENTS IN A RADIATION THERAPY ENVIRONMENT, and U.S. Pat. No. 7,199,382, issued on Apr. 3, 2007, titled PATIENT ALIGNMENT SYSTEM WITH EXTERNAL MEASUREMENT AND OBJECT COORDINATION FOR RADIATION THERAPY SYSTEM, the contents of each of which are hereby incorporated in their entirety into this disclosure by reference.

B. Modular Patient Support System:

In accordance with the one embodiment described herein, there is provided a modular patient support system that generally comprises a modular patient pod and an immobilization device.

Figure 4A:
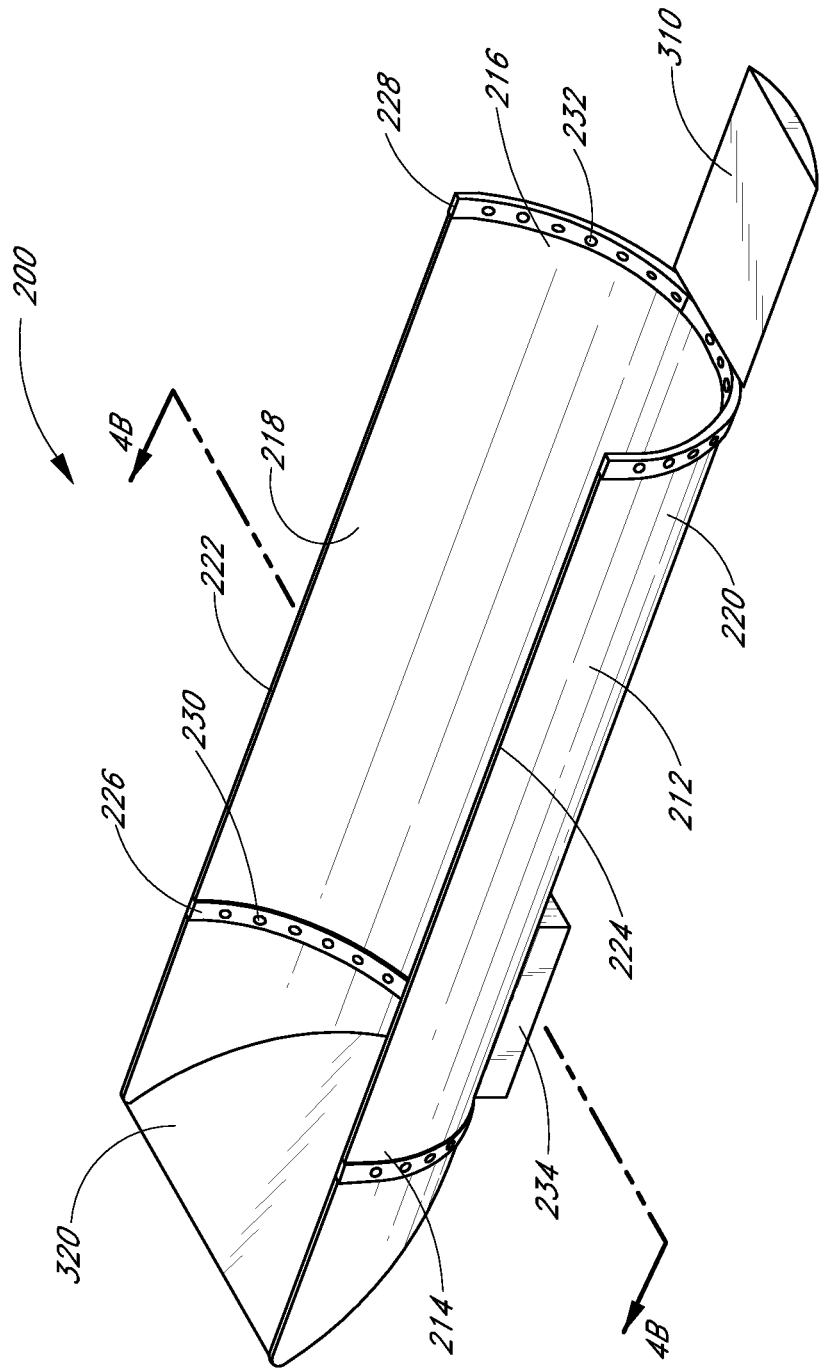
FIG. 4A is an isometric elevated side view of one embodiment of a modular patient pod.

FIGS. 4A and 4B illustrate one embodiment of a modular patient pod 200 for radiation therapy. The pod 200 comprises a longitudinally extending shell structure 212. In the present embodiment, the positioner-pod connector 234 is offset from the middle of the shell structure 212, thereby resulting in a pod 200 that is cantilevered with respect to the working end 116 of the patient positioner 114. A pod 200 that is cantilevered with respect to the positioner 114 advantageously allows more ways to position the patient within the radiation therapy system 100. A cantilevered pod 200 advantageously reduces the chances of collisions with other components of the system 100 as the pod 200 and/or positioner 114 or adjusted within the system 100. A pod 200 that is cantilevered can also facilitate the entry or placement of the patient into the pod 200. In another embodiment (not illustrated), the connector 234 is located, along the longitudinal axis of the pod 200, at or near the middle of the shell structure 212.

The pod 200, any components thereof, and any extensions or attachments thereto, are described herein with reference to the section of the pod 200 which interfaces with the patient positioner 114 via a positioner-pod connector 234. Any components, extensions, and attachments that are closer, along a visualized longitudinal axis of the pod 200, to the connector 234 are referred to herein as being proximal, while any components, extensions, and attachments located toward the opposite end of the pod are referred to herein as being distal.

The longitudinally extending shell structure 212 extends between a shell proximal edge 214 and a shell distal edge 216. The shell 212 has a transverse concave top surface 218 and a transverse concave bottom surface 220. The shell 212 transversely extends between a first upwardly-extending lateral edge 222 and a second upwardly-extending lateral edge 224.

With reference to FIGS. 4A and 4B, in one embodiment, the support shell 212 is a hemi-cylindrical structure acting as a cantilevered support for patients during radiation treatment. Here, the hemi-cylindrical shape of the shell 212 facilitates providing enhanced physical support and consistent indexing when used with immobilization devices, such as, for example, foam inserts or vacuum bags, described in further detail below. The curved shape of the pod 200 also permits beam shaping devices to be located near the patient.

The patient can be positioned in the patient pod 200 in any number of positions. In one approach, where the patient is positioned in the pod 200 in a supine position with his head near the shell distal edge 216 and his feet near the shell proximal edge 214, the lateral edge 222 is on the patient's right-hand side while the lateral edge 224 is on the patient's left-hand side. In another approach, where the patient is positioned in the pod 200 in a prone position with his head near the shell distal edge 216 and his feet near the shell proximal edge 214, the lateral edge 222 is on the patient's left-hand side while the lateral edge 224 is on the patient's right-hand side. In yet another approach, where the patient is positioned in the pod 200 in a supine position with his feet near the shell distal edge 216 and his head near the shell proximal edge 214, the lateral edge 222 is on the patient's left-hand side while the lateral edge 224 is on the patient's right-hand side.

With reference to FIGS. 4A and 4B, in one embodiment the pod 200 comprises attachment or extension tracks 226 and 228 that are located on shell edges 214 and 216, respectively. Extension tracks 226 and 228 can comprise a known universal attachment mechanism, such as, for example, a plurality of linearly arranged apertures 230, 232 that facilitate communication between the top and bottom surfaces 218, 220 of the shell 212. In one embodiment, one or more modular extensions are adjustably fastened to the attachment tracks 226, 228 by means of removable pins or bolts slotted or screwed through the apertures 230, 232.

In one method of use, involving treatment near the patient's head region, the patient is positioned with his head beyond shell edge 216 on a head rest extension 310 attached to track 228. In another method of use, involving treatment in the patient's lung region, the patient is positioned head-first (i.e., head near shell edge 216) with his shoulders inline with track 228 so that the radiation beam passes through the shell 212 and into the lung region. In yet another method of use, involving treatment in the patient's lung region, the patient is positioned head-first with his shoulders beyond the track 228 so that treatment occurs outside the shell 212.

As used herein, negative pitch refers generally to the lowering or dipping of the pod 200 distal end, while positive pitch refers generally to the raising of the pod 200 distal end. Negative roll refers generally to the counterclockwise rotation of the pod 200, while positive roll refers generally to the clockwise rotation of the pod 200. Negative yaw refers generally to the rotation of the pod 200 about Axis-6 to the left, while positive yaw refers generally to the rotation of the pod 200 about Axis-6 to the right.

The shell 212 is preferably sufficiently long and wide to receive most or all of the body of a human patient lying on it in any position, such as, for example, the supine or prone positions. The structural shell 212 length from Axis-6 to the distal edge 216 without attachments is typically in the range of about 75 cm to about 175 cm, often about 80 cm to about 125 cm, depending on the intended patient application specific size (e.g., pediatric) and/or gantry size. In one embodiment, the length of the shell 212 from Axis-6 to the distal edge 216 is on the order of 90 cm. As used herein, Axis-6 refers to the axis of the positioner 114 that extends vertically through the attachment at the final yaw axis (e.g., wrist) of the positioner 114 (e.g., in the embodiment shown in FIGS. 2 and 3, the wrist comprises the swivel joint 152 at the distal end 116 of the robotic arm 150), thereby allowing yaw rotation of the patient pod 200.

The overall longitudinal length of the shell 212 (i.e., between shell proximal edge 214 and shell distal edge 216) is typically in the range of about 90 cm to about 235 cm, often about 95 cm to about 175 cm. In one embodiment, the overall longitudinal length of the shell 212 is about 106 cm. The outer diameter of the shell 212 is typically in the range of about 35 cm to about 65 cm, often about 35 to about 55 cm depending on the intended patient application specific size (e.g., pediatric, large patient, etc.) and/or available treatment energy. In one embodiment, the outer diameter of the shell 212 is about 46 cm.

In one embodiment, the shell 212 has a non-metallic (e.g., carbon fiber) composite construction that facilitates radiation beam treatments through the shell 212. Any number of imaging simulators known in the art (e.g., computed tomography imaging (CT), positron emission tomography (PET), magnetic resonance imaging (MRI), cone beam imaging. etc.) can be used to account for the treat-through material of the shell 212. As used herein, the term "treat-through" refers generally to physical property of a material or surface that allows radiation beams to be irradiated through a surface, and thereby deliver prescribed radiation doses from a radiation source, through a surface, and into a targeted area within the patient on the other side of the surface. Treat-through properties are generally measured or quantified in terms of molecular equivalence of water. As used herein, the term "non-treat through" refers generally to the physical property of a material or surface that does not allow radiation beams to be irradiated through a surface. Areas of the shell 212 made of non-metallic materials are generally referred to as treat-through surfaces or zones.

As used herein, water equivalency refers generally to the effect of an absorbing material on proton beam range relative to water. With respect to the treat-through sections, zones, or surfaces described herein, water equivalency is measured with respect to radiation beams that are perpendicular to the penetrable surface.

In one embodiment, illustrated in FIG. 4C, the shell 212 comprises a core material 240 encapsulated in a structural skin 242. The core material 240 can comprise any suitable low density materials known in the art, such as, for example, structural foam or the like. The structural skin 242 can comprise any suitable firm, lightweight material known in the art, such as, for example, carbon fiber, spectra fiber, etc.

U.S. Provisional Application No. 60/583,063, filed Jun. 25, 2004, titled METHOD AND DEVICE FOR REGISTRATION AND IMMOBILIZATION, the disclosure of which is hereby incorporated in its entirety herein by reference, discloses some suitable materials from which the shell 212 can be constructed.

In one embodiment, the shell 212 is made from polyvinylchloride (PVC) or the like. In another embodiment, the shell 212 is made from fiberglass or the like. In still another embodiment, the shell 212 comprises any known suitable low density foam or the like.

In one embodiment, the shell 212 is constructed of composite skins comprising polyethylene fibers embedded in an epoxy resin and a low-density polystyrene foam (Styrofoam®) core. A list of some of the materials that can be used in manufacturing the shell 212 appears in Table I below.

| # | Matrix | Fiber Type | Fiber Structure |
|---|---|---|---|
| 1 | high impact polystyrene (HIPS) | none | n.a. |
| 2 | polymethylmethacrylate (PMMA) | none | n.a. |
| 3 | polycarbonate (PC) | none | n.a. |
| 4 | polyvinylchloride (PVC) | none | n.a. |
| 5 | polyethylene (PE) | none | n.a. |
| 6 | epoxy resin | none | n.a. |
| 7 | epoxy resin | fiberglass | random |
| 8 | epoxy resin | fiberglass | woven |
| 9 | epoxy resin | aramid | woven |
| 10 | epoxy resin | UHMW PE | unidirectional tape |
| 11 | epoxy resin | carbon | twill woven |
| 12 | epoxy resin | carbon | unidirectional tape |
| 13 | epoxy resin | ultrahigh modulus carbon | unidirectional tape |

In one embodiment, the carbon fiber composites, each woven ply of a lay-up is approximately 0.25 mm thick. In one embodiment, the composite lay-up is approximately 50% fiber and 50% resin by weight. In one embodiment, the fiber content of the composite is maximized while the resin content is minimized. In one embodiment, the shell 212 of the pod 200 is made from the composite material Spectra, which is available from Honeywell Performance Fibers in Colonial Heights, Va.

In one embodiment, at least one of the extension tracks 226, 228 is made from any suitable metal known in the art, such as, for example, aluminum. The use of metal, however, results in non-treat through zones or areas. As such, the use of metal structures is generally limited in order to minimize non-treat through surfaces. In another embodiment, at least one of the tracks 226, 228 is made from a suitable non-metal material known in the art, such as, for example, a carbon composite.

The extension tracks 226, 228 are advantageously positioned at the shell edges 214 and 216 of the pod 200, thereby facilitating radiation treatment through the support shell 212 of the pod 200. The positioning of the extension tracks 226, 228 at the shell edges 214, 216 also facilitates the attachment of one or more pod extensions to the pod 200 as explained in further detail below.

In one embodiment, the extension tracks 226, 228 are rounded such that for certain treatment positions, the patient shall not experience pain or discomfort as the result of his contact with the track 226 or 228. The extension tracks 226, 228 preferably comprise interface extensions that are approximately flush with the inside surface 218 of the shell 212. In one embodiment, the maximum step or vertical distance between the inner surface 218 and the track interface extension is about 1 cm.

Extension tracks 226, 228 allow one or more pod extensions to be connected to the pod 200, and provide modularity to the overall design. For example, track 228 can accommodate multiple head extensions and allows for 2-pi head and neck treatments. The modularity of the pod components and optional pod extensions accommodate multiple patient positions within the pod 220, such as, for example, both head-first and feet-first treatment positions. The pod 200 also accommodates treatment positions where the patient lies on his back, side, stomach, or any variations thereof. It will be noted that actual position of the patient within the pod 200 will depend on various factors, such as, for example, the radiation treatment protocol, as determined by the physician and/or radiation physicist, and the physical characteristics of the patient.

Figure 6:
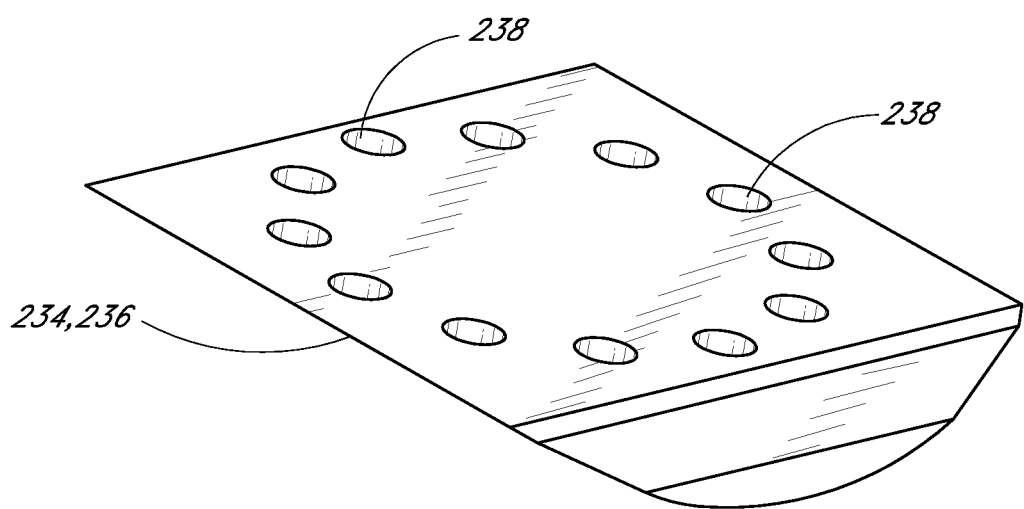
FIG. 6 is an isometric elevated side view of one embodiment of a positioner-pod connector.

With reference to FIGS. 4A, 4B, and 6, in one embodiment, positioner-pod connector 234 is a rigid base member that allows connection to any patient positioner 114, such as, for example, via the distal, working end 116 of the positioner 114. The connector 234 comprises a positioner interface clamping plate 236 for interfacing and attaching the pod 200 to the patient positioner 114. The clamping plate 236 comprises a plurality of female ends 238 arranged in a circular pattern for receiving bolts or other suitable fastening devices, thereby fixedly securing the pod 200 to the positioner 114. This particular embodiment of the clamping plate 236 is well suited for accommodating the bolt pattern available on the KUKA KR500-L420 robotic positioner.

In one embodiment, the connector 236 (e.g., clamping plate) protrudes into the shell 212 with a height H of approximately 1.75 inches, extends longitudinally L along the shell 212 approximately 12 inches over the robot connection, and has a width W of approximately 11 inches. In another embodiment (not shown), the connector is integrated into the shell 212 and is flush to the contour of the inside surface of the shell 212.

It will be noted that the pod 200 and any mechanical device mounted thereto should be positioned to avoid collision with the positioner 114 during yaw treatment angles. The distance between the inside surface 218 of the shell 212 and the connector 234 is typically in the range of about 5 mm to about 35 mm, often about 12 mm to about 25 mm. In one embodiment, the distance between the inside surface 218 of the shell 212 and the connector 234 is about 19 mm.

The patient pod 200 can comprise one or more attachments, extensions, adapter plates, or the like, or combinations thereof (collectively, "pod attachments"). In one embodiment, shown in FIG. 4A, the pod 200 comprises a cantilevered head rest extension 310 and a robot end, foot rest extension 320. In another embodiment, shown in FIG. 2, the pod 200 comprises a supine head extension 258 and a robot end extension 320.

With reference to FIGS. 7A-7G, one or more pod attachments can be removably attached to one or both of the pod extension tracks 226, 228. In one embodiment, no tool is required to attach or remove the pod attachments to the extension tracks 226, 228 of the pod 200. The pod attachments preferably comprise treat-through materials and surfaces.

While these pod attachments can have treat-through surfaces that vary in water equivalent thickness, it is preferred that the treat-thought surfaces not vary in water equivalent thickness with a gradient greater than about 0.5 mm water equivalent thickness/mm along any transverse distance. The gradient limits will define design edge effects, thickness changes, and material transitions, as well as general manufacturing tolerances such as voids and material surface imperfections. In one embodiment, the attachments have water equivalencies of no more than about 2 cm. In one embodiment, the shell 212 has about a 25 mm wide non-treat through region due to the mounted attachment track 226 or 228. It will be noted that the certain embodiments where the tracks 226, 228 are made of metal, the tracks are non-treat through, whereas in certain other embodiments where the tracks 226, 228 are made of non-metal materials, such as, for example, carbon fiber, the tracks 226, 228 provide treat-through zones. As with the shell 212, certain pod attachments can comprise up to about a 25 mm wide non-treat through region due to the tracks 226, 228.

With reference to the embodiments shown in FIGS. 7A-7G, each of the pod attachments 270, 280, 290, 300, 310, 320, 330 comprise an extension track engaging end 262 which interfaces and connects with extension tracks 226 and/or 228. The track engaging end 262 comprises an upper lip 264 and a lower lip 266, where the space between lips 264 and 266 is approximately equal to the distance between the inner and outer diameters of extension tracks 226 and 228. The upper and lower lips 264 and 266 each comprise a plurality of apertures 268, where each upper lip aperture is aligned with a corresponding lower lip aperture along a visualized radius extending outward from the center of the hemi-cylindrical shell 212. In one embodiment, the apertures 268 are drilled or molded into locations within the track engaging end 262 to align with the extension track apertures 230 or 232 along a visualized radius extending outward from the center of the hemi-cylindrical shell 212 when the track engaging end 262 engages with tracks 226 or 228. In one embodiment, the attachment 270 is adjustably fastened to attachment track(s) 226 or 228 by means of removable pins, bolts, or equivalents thereof, slotted or screwed through the radially aligned apertures 230, 232, 268.

Figure 7A:
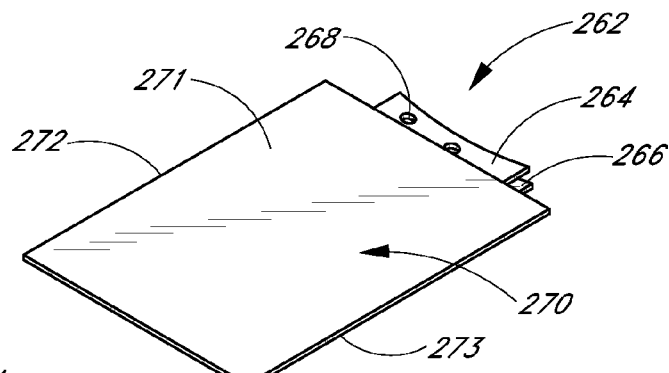
FIG. 7A is an isometric elevated side view of one embodiment of one embodiment of a short, flat attachment.

With reference to FIG. 7A, in one embodiment, the pod attachment comprises a short, flat attachment 270 with a length of about 30 cm and a width of about 23 cm. Attachment 270 facilitates positioning the patient at isocenter for head treatment including vertex with minimal shoot through material and permits 5-degree pitch and roll corrections. Attachment 270 comprises treat-through section 271 and treat-through edges 272, 273.

Figure 7B:
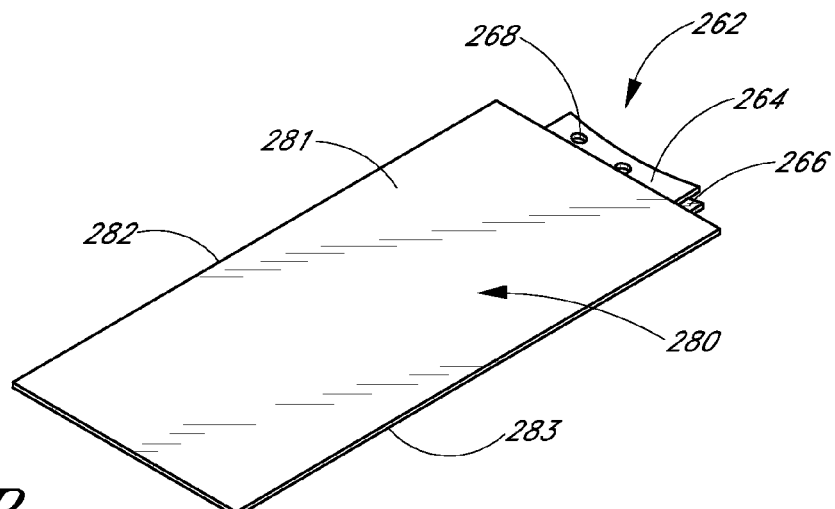
FIG. 7B is an isometric elevated side view of one embodiment of a long, flat attachment.

With reference to FIG. 7B, in one embodiment, the pod attachment comprises a long, flat attachment 280 with a length of about 48 cm and a width of about 23 cm. Attachment 280 facilitates positioning the ENT/shoulder region away from the any non-treat through pod attachment tracks 226, 228. Attachment 280 comprises treat-through section 281 and treat-through edges 282, 283.

Figure 7C:
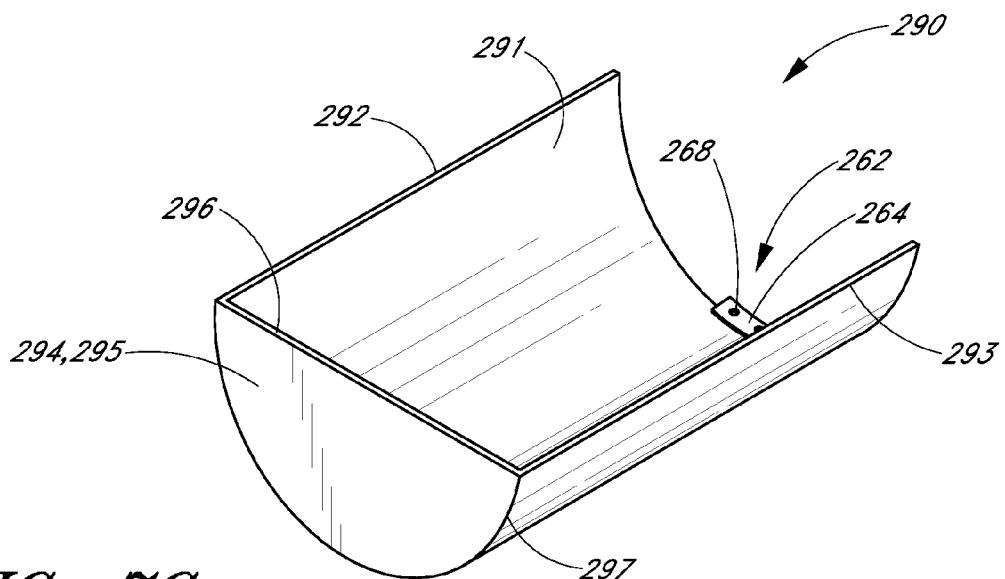
FIG. 7C is an isometric elevated side view of one embodiment of a shell leg or head extension.

With reference to FIG. 7C, in one embodiment, the pod attachment comprises a shell leg or head extension attachment 290 that has a diameter approximately the same as the pod shell 212 and that is approximately 67 cm long, thereby allowing the pod 200 to accommodate patients who are 75 inches tall. Attachment 290 comprises an end-stop or cap 294 against which the patient's feet can be placed. Attachment 290 comprises treat-through section 291, treat-through edges 292, 293, non-treat through section 295 and non-treat through edges 296, 297.

Figure 7D:
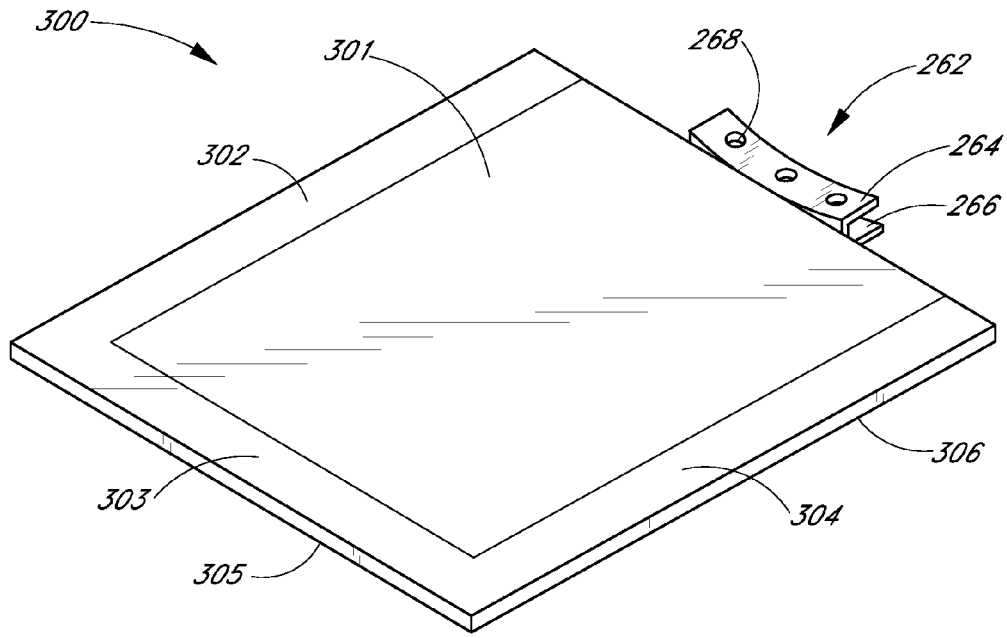
FIG. 7D is an isometric elevated side view of one embodiment of a flat extension that accommodates immobilization devices.

With reference to FIG. 7D, in one embodiment, the pod attachment comprises a flat extension 300 that is about 40 cm long and about 36 cm wide. Extension 300 comprises treat-through section 301, non-treat through sections 302, 303, 304, and non-treat through edges 305, 306. Here, section 301 is a head-rest region, while sections 302, 303, 304 makeup the immobilization device attachment region. In one embodiment, extension 300 accommodates any number of immobilization devices and techniques, described in further detail below. For example, in one embodiment, extension 300 can be dimensioned to facilitate optional cranial ring immobilization mountings.

Figure 7E:
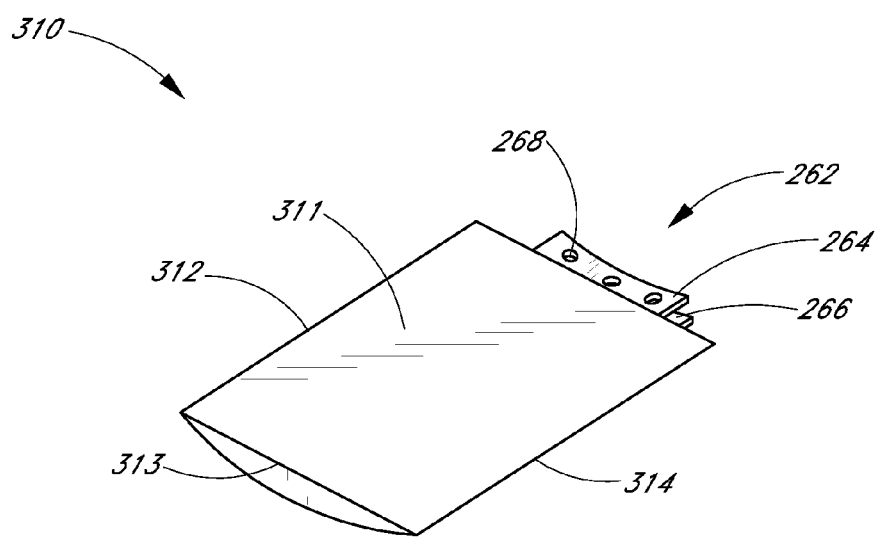
FIG. 7E is an isometric elevated side view of one embodiment of a short, head rest extension.

With reference to FIG. 7E, in one embodiment, the pod attachment comprises a short, head rest extension 310. Extension 310 comprises treat-through section 311 and treat-through edges 312, 313, 314.

Figure 7F:
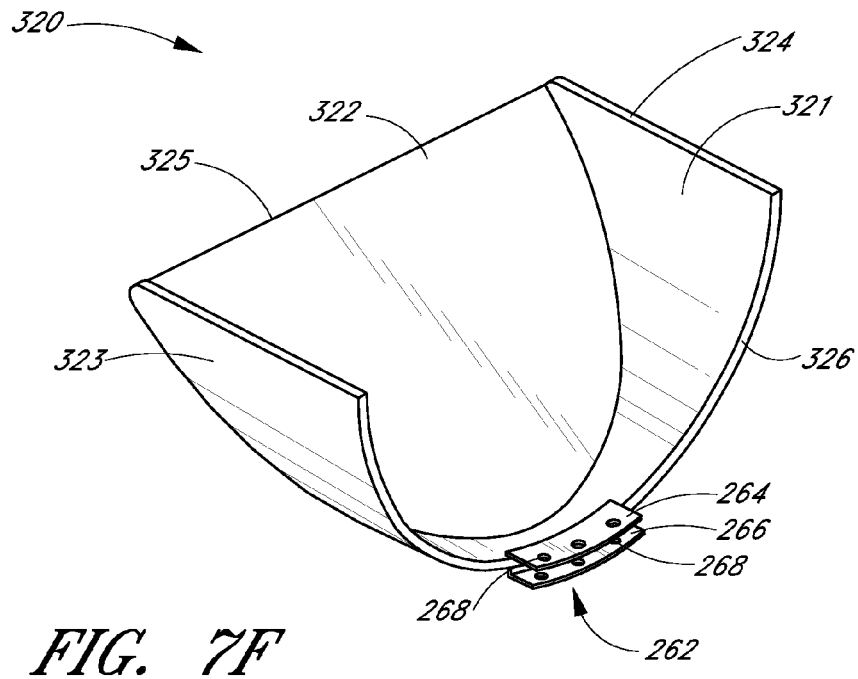
FIG. 7F is an isometric elevated side view of one embodiment of a positioner end extension.

With reference to FIG. 7F, in one embodiment, the pod attachment comprises a robot end extension 320 that is chamfered at an angle of approximately 45-degrees relative to a visualized, longitudinal axis extending between the proximal and distal extension tracks 226 and 228, beginning at about 19 cm from Axis-6 up to distance of about 43 cm from Axis-6, thereby preventing collision with the patient positioner 114. Extension 320 does not have any treat-through sections or edges; rather, sections 321, 322, 323 and edges 324, 325, 326 are all non-treat through.

Figure 7G:
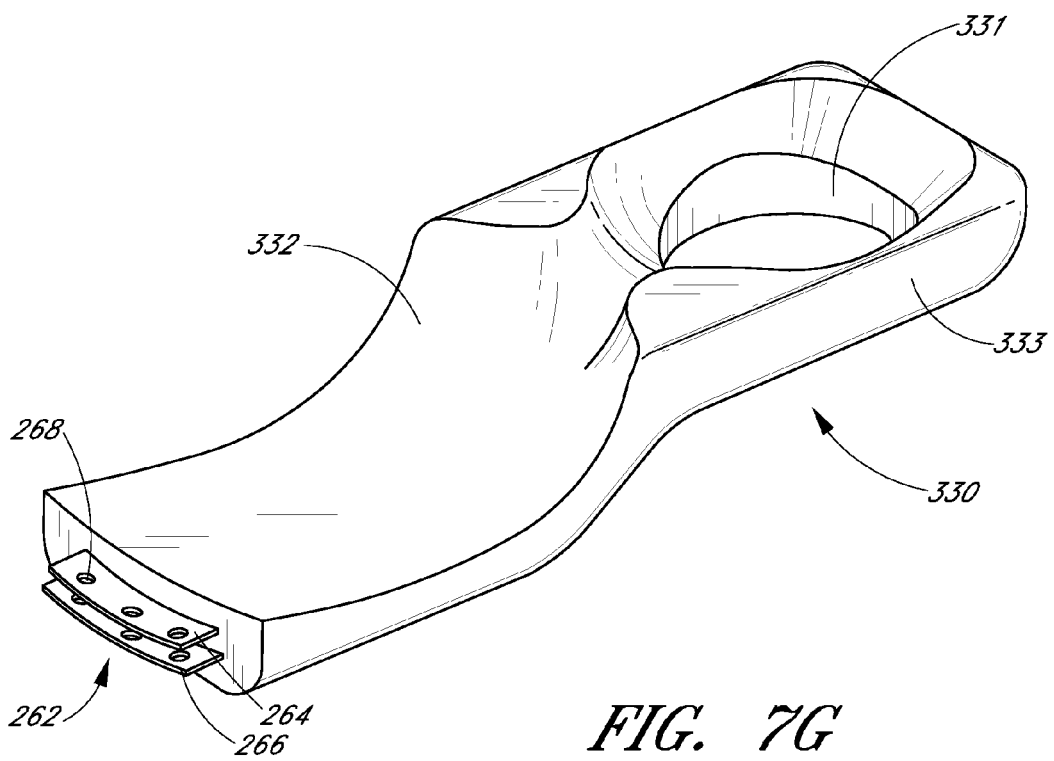
FIG. 7G is an isometric elevated side view of one embodiment of a prone headrest.

With reference to FIG. 7G, in one embodiment, the pod attachment comprises a prone headrest 330 to accommodate prone treatments. The prone headrest defines an face-through hole 331 through which the patient can place his face. The prone headrest 330 comprises non-treat through sections 332, 333.

Any number of immobilization devices can be used with the patient pod 200. With reference to FIG. 5, in one embodiment, the modular patient support system 199 comprises the patient pod 200 and an immobilization device, further comprising a rigid moldable foam cradle 350 bonded to the pod shell top surface 218. Cradle 350 conforms to a selected region (e.g., back, front, or side) and comprises a mold 352 conforming exactly to the patient's body for securely holding the patient in position during radiation treatments. The rigid foam cradle 350 can be formed in a manner similar to that employed in U.S. Pat. No. 4,905,267, titled METHOD OF ASSEMBLY AND WHOLE BODY, PATIENT POSITIONING AND REPOSITIONING SUPPORT FOR USE IN RADIATION BEAM THERAPY SYSTEMS, the disclosure of which is hereby incorporated in its entirety herein by reference.

In one approach, an expandable, liquid foaming agent known as ACMM foaming agent 325, available from the Soule Co., Inc., Lutz, Fla. or Smithers Medical Products, Inc., Akron, Ohio, is used to form the rigid foam cradle 350. In one approach, the foaming agent is painted onto the shell top surface 218. After the foaming agent is introduced within the shell, the patient is positioned within the shell where he lays motionless for approximately 15 minutes until the foaming agent has cooled to room temperature and the patient body mold 352 is formed.

The foam between the patient and the pod can be mechanically stabilized to prevent the foam from moving and displacing the patient between or during treatments. In one approach, the foam is placed inside a very thin plastic bag. In another approach, the pod is lined with a low-density foam sheet. In still another approach, a very thin, disposable, plastic shell is inserted into the pod before applying the foam chemicals. In yet another approach, there is no lining between the foam and pod; rather, the inner pod surface is made very smooth by the composite layers on a high quality aluminum mold. In still another approach, the inner surface of the pod is coated with Teflon or another nonreacting substance.

Other suitable immobilization devices that can be used with the patient pod 200, with or without any flat extensions, include, but are not limited to, bite blocks, face masks, vacuum bags, halos or cranial rings, localizer Z-frame boxes, triangular leg pillows, foam inserts, or the like, or combinations thereof. Bite block mouthpieces are preferably compatible with any existing MRI "Head Coils." In one embodiment, the bite block frame preferably limits translational movement of any point in the treatable volume to no more than about 1.0 mm given the force of 30 pounds in any direction. In another embodiment, the bite block frame limits head rotations to less than or equal to about one-degree in any direction under a force of about 30 pounds in any direction. In one embodiment, the bite block frame mounts to the shell 212 and/or any pod attachments via an existing vacuum system providing approximately 9 psi.

With respect to the various pod attachments described above, the weight of any of the pod attachments preferably does not exceed about 30 pounds in weight, thereby making it easier for an individual to carry and install the pod attachment to the pod shell 212. Pod attachments mounted on the side near Axis-6 are preferably angled along the robotic arm or positioner to eliminate injury or collision.

In one embodiment, the pod 200 is capable of supporting a 400 pound distributed patient load (not including any immobilization devices) with the patient center of gravity not to exceed 37 inches from Axis-6. The pod 200 is preferably capable of supporting a 300 pound end load (with or without extensions) to accommodate an individual seated on the cantilevered end 216. In one embodiment, the pod 200 is capable of supporting a patient load of 300 lbf, an immobilization load of 50 lbf, and a 200 lbf longitudinal load located on the extensions.

In one embodiment, the pod 200 is preferably capable of supporting a water phantom load of 275 pounds (125 kg) at the proximal extension track 226.

In one embodiment, the pod 200 is capable of supporting an immobilization and patient load of up to approximately 150 pounds located on the attachments with a deflection of no more than 2 mm. Extensions are preferably capable of supporting a 300 pound load at the end in the event a person was to sit on the extension, thereby resulting in a pod with extension that is not overly flexible.

With continued reference to FIGS. 4A and 4B, in one embodiment, the deflection of the shell 212 at the cantilevered end 216 due to patient load is preferably less than or equal to about 5 mm. In one embodiment, such deflection can be compensated for during treatment using an external measurement system that will correct inherent mechanical errors. In one embodiment, the pod 200 is accompanied by or includes an inclinometer as safety feature to prevent the positioner 114 from producing angular deflections great than about ±5.5 degrees from the horizontal. An inclinometer or tilt sensor comprises any device, typically electro-mechanical, that senses the angle of an object with respect to gravity.

The vertical deflection of the patient pod 200 at the distal, cantilevered end (with or without extensions) due to a 300 pound patient distributed load and 50 pound immobilization load is preferably less than about 4 mm. The lateral deflection of the pod 200 (with or without extensions) due to a patient lateral load of 100 pounds is preferably less than about 0.5 mm. It will be noted that these types of vertical and lateral deflections can be compensated for during treatment by using an external measurement system that corrects inherent mechanical errors.

All table constituent materials and components preferably withstand an average daily radiation dose of approximately 9,000 rads, 5 days per week, 52 weeks per year, over a 20 year lifetime. All hardware and components preferably operate normally in the temperature environment of 40-95 degrees F. with a relative humidity of 25-78%.

The treat-through surfaces of the pod 200 preferably do not vary in thickness with a gradient greater than about 0.5 mm water equivalent thickness per mm along any transverse distance. The edges of treat-through areas of the pod 200 are preferably less than about 0.5 mm water equivalent thickness. In one embodiment, the treat-through thickness of the pod 200 preferably has a water equivalency of less than approximately 2 cm.

Components of the pod 200 positioned between the patient and the radiographic image receptor preferably have an aluminum equivalence less than or equal to about 5 mm per FDA CFR part 1020.

With continued reference to FIGS. 4A and 4B, in one embodiment, the geometry and size of the pod 200 accommodates a CT scanner with a physical aperture of 68 cm and an image reconstruction diameter of 48 cm. The treat-through surfaces in the shell 212 preferably do not vary in thickness. Here, the edges of treat-through areas are preferably less than about 0.5 mm water equivalent thickness. In one preferred embodiment, the thickness of the shell 212 has a water equivalency of no more than about 2 cm.

The pod attachments preferably have an aluminum equivalence of about 5 mm per FDA CFR Part 1020 (Compliance determined by x-ray measurements made at a potential of 100 kilovolts peak and with an x-ray beam that has a HVL of 2.7 mm of aluminum). As used herein, aluminum equivalency refers to the thickness of aluminum (type 1100 alloy) affording the same radiographic attenuation, under same specified conditions, as the material in question. It will be noted that the modular patient support system 199 is preferably capable of accommodating a 65 cm×60 cm×60 cm water phantom at the robot end.

In one embodiment, the radiation treatment system 100 comprises an external measurement or vision system, which further comprises vision system markers. The vision system markers are preferably mounted to the non-treat through areas, such as, for example, tracks 226, 228 made of metal.

C. Patient Pod with Tapered Edge Configuration

In accordance with one embodiment described herein, there is provided a patient pod with a tapered edge configuration that reduces edge effects associated with abrupt changes in the water equivalency in the radiation beam path.

For certain radiation treatment protocols, radiation beams of a prescribed intensity are delivered from lateral positions. In certain instances, for example, where the radiation beam is delivered from a lateral position that is well above patient pod, the radiation beam does not have to be delivered through the patient pod. In another scenario, where the radiation beam is delivered from a lateral position that is well below the patient pod, the radiation beam can pass through a pod shell surface of uniform density or water equivalency. There are situations, however, where the radiation beam traverses one or both of the lateral edges (e.g., lateral edge 222 or 224 of the pod shell 212 depicted in FIG. 4A). An abrupt transition or change in the water equivalency between the pod shell and the space above the pod shell lateral edge can result in radiation beams having intensities that are non-uniform or difficult to predict. The effects of any abrupt transitions in the water equivalency in the beam path referred to herein as edge effects.

Sections of the lateral edges of the patient pod can be tapered to reduce or minimize the edge effects. With reference to FIG. 4C, in one embodiment, the lateral edge 222 comprises a gradually tapered edge 243 and a longitudinally-extending rail 299. The tapered edge 243 comprises an inner surface 245 that tapers outward beginning at lower edge 244 and ends at upper edge 248. Tapered edge 243 also comprises an outer surface 247 that tapers inward beginning at lower edge 246 and ends at upper edge 248. Surfaces 245 and 247 ultimately converge at upper edge 248. The location and degree of tapering of edges 244, 246 can be varied as needed to reduce any edge effects.

With reference to FIGS. 4A-4C, the tapered edge 243 is typically tapered with a gradient from about 0.1 mm water equivalency/mm to about 5 mm water equivalency/mm, depending on accuracy requirements and repeatability of immobilization devices. In one embodiment, the tapered portion 243 is tapered with a gradient of about 0.5 mm water equivalency/mm.

The lateral edges of the pod are relatively thin, thereby minimally perturbing any therapeutic proton beams passing through or near any of the lateral edges.

The low-density rail 299 covers tapered edge 243, and thereby protects the patient and radiation treatment providers from the upper edge 248 which tends to be a sharp edge. With reference to exemplary shell lateral edge 222 illustrated in FIG. 4C, the lateral edge 222 generally comprises an inferior portion that is complementary to the shape of the tapered edge 243 and a superior portion that is generally rounded or blunt.

The rail 299 preferably comprises a low-density material, such as, for example, epoxy with microspheres, extruded or molded plastics (nylon, urethane, etc.), rubber, or the like, or combinations thereof. In one embodiment, the rail 299 maintains the 0.5 mm/mm water equivalent gradient of the shell 212.

In one embodiment, the rail 299 is removably secured to the shell tapered edge 243 via any attachment mechanism known in the art, such as, for example, an interlocking receiver molded into the shell 212 for positive locating and holding of the rail 299. In another embodiment, the rail 299 simply sits the tapered edge 243 without the aid of any attachment mechanisms. In yet another embodiment, the rail 299 is permanently secured to the tapered edge 243 using any known suitable attachment mechanism, such as, for example, epoxy with micro-spheres. Patient safety and comfort are preferably integrated with each embodiment. Several transitions, methods, and materials can be used to achieve specified gradient, level of safety and patient comfort, such as, for example, replaceable handrails or pliable edges.

D. Aimable Volume of Modular Patient Support System

The aimable volume will generally depend on the orientation of the patient pod 200 and the patient positioner 114 that interfaces with the patient pod 200 along the orthogonal translational and rotational axes.

Figure 8:
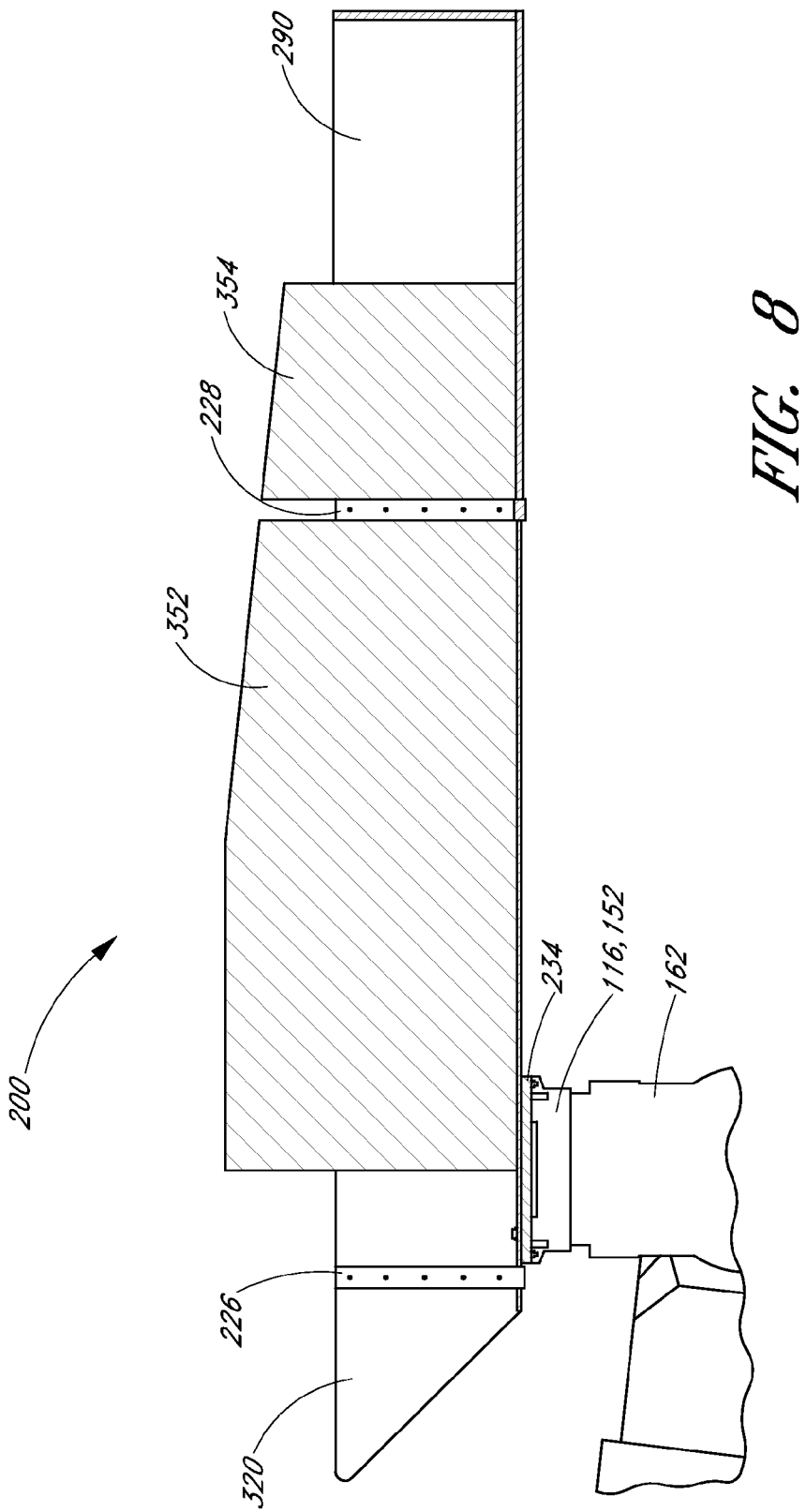
FIG. 8 is a schematic partial cross-sectional side view of one embodiment of a modular patient support system and corresponding aimable volumes.

FIG. 8 provides a schematic partial cross-sectional side view of the shape of the aimable volumes 352, 354 (hashed) for the pod shell 212. Here, the pod 200 has a thickness of about 1.9 cm above the positioner-pod connector 234. For any yaw angle up to 93 degrees, with or without pitch and roll corrections, the aimable volume (made up of volumes 352 and 354) is approximately a 40 cm tall by 50 cm wide trapezoidal volume extending about 120 cm along the table from Axis-6 to a distal height of about 31.9 cm. One half of the aimable volume is accessible in 93-degree vertex positions when the bottom of the aimable volume is at isocenter. For example, in one embodiment, in a left vertex position at a 93-degree yaw, the left half of a patient's head (positioned face up with head at end of pod 200) is inaccessible because of maximum robot reach. Positioning the pod 200 to a right vertex allows accessibility to this left half. The patient himself may be positioned with a lateral shift to eliminate this. Here, the aimable volumes 352, 354 for vertex treatments typically begin about 3 cm off of shell surface 218.

It will be understood that the invention described herein, and the component parts thereof, can be sued in any number of combination of treatment systems, including, but not limited to, proton treatment, conventional radiation treatment, and imaging systems (e.g., CT, PET, MRI, cone beam, etc.).

While the present invention has been illustrated and described with particularity in terms of preferred embodiments, it should be understood that no limitation of the scope of the invention is intended thereby. Features of any of the foregoing devices and methods may be substituted or added into the others, as will be apparent to those of skill in the art. The scope of the invention is defined only by the claims appended hereto. It should also be understood that variations of the particular embodiments described herein incorporating the principles of the present invention will occur to those of ordinary skill in the art and yet be within the scope of the appended claims.

What is claimed is:

1. A patient pod configured to support a patient during a medical treatment, the pod comprising:
    a semi-cylindrical shell structure configured to be concave upward to provide a patient space, the shell structure extending transversely between a first lateral edge and a second lateral edge and extending longitudinally between a proximal edge and a distal edge, the shell structure comprising a top, concave surface and a bottom, convex surface that faces outward, away from the patient space;
    the top, concave surface configured to be parallel to the bottom, convex surface, except at the first and second lateral edges;
    the first and second lateral edges being tapered to reduce the effect of changes in the water equivalency between the shell structure and a space above the shell structure;
    the top, concave surface comprising a separate, flat, inwardly-facing portion that tapers away from the top, concave surface of the shell structure to a narrower upper tip,
    the bottom, convex surface comprising a separate, flat, outward facing portion that tapers away from the bottom, convex surface and converges to meet the flat, inwardly-facing portion at the narrower upper tip.

2. The patient pod of claim 1, further comprising:
    a proximal extension track configured for engagement with any of a number of proximal pod attachments in order to extend the shell structure from the proximal edge; and
    a distal extension track configured for engagement with any of a number of distal pod attachments in order to extend the shell structure from the distal edge.

3. The patient pod of claim 1, wherein the separate, flat, inwardly-facing portion that tapers away from the top, concave surface of the shell structure to a narrower upper tip and the bottom, convex surface comprising a separate, flat, outward facing portion that tapers away from the bottom, convex surface together comprise a tapered section of the patient pod.

4. The patient pod of claim 3, wherein the patient pod further comprises at least two tapered sections.

5. The patient pod of claim 3, wherein the tapered section is tapered with a gradient from about 0.1 mm water equivalency/mm to about 5 mm water equivalency/mm.

6. The patient pod of claim 3, wherein the tapered section is tapered with a gradient of about 0.5 mm water equivalency/mm.

7. The patient pod of claim 3, further comprising a longitudinally-extending rail configured to cover the tapered section.

8. A patient support configured to position a patient during a medical treatment, the support comprising:
    a shell extending in a transverse direction between a first tapered lateral edge and a second tapered lateral edge and extending in a longitudinal direction between a proximal edge and a distal edge, the shell comprising a top, concave surface and a bottom, convex surface;
    the first tapered lateral edge comprising a first separate, flat, inwardly-facing portion that tapers away from the top, concave surface of the shell to a first narrower upper tip and a first separate, flat, outward facing portion that tapers away from the bottom, convex surface of the shell and converges with the first flat, inwardly-facing portion at the first narrower upper tip; and the second tapered lateral edge comprising a second separate, flat, inwardly-facing portion that tapers away from the top, concave surface of the shell to a second narrower upper tip and a second separate, flat, outward facing portion that tapers away from the bottom, convex surface of the shell and converges with the second flat, inwardly-facing portion at the second narrower upper tip.

9. The patient support of claim 8, further comprising a first rail configured to cover the first tapered lateral edge and a second rail configured to cover the second tapered lateral edge.

10. The patient support of claim 9, wherein the first rail and the second rail have a water equivalent thickness of about 0.5 mm of water at locations where a radiation beam passes through.

11. The patient support of claim 9, wherein the first rail comprises an inferior portion that is complementary in shape to the first tapered lateral edge and the second rail comprises an inferior portion that is complementary in shape to the second tapered lateral edge.

12. The patient support of claim 9, wherein the first rail and the second rail each comprise a superior portion that is rounded.

13. The patient support of claim 9, wherein the first rail and the second rail comprise at least one of epoxy, nylon, urethane, and rubber.

14. The patient support of claim 8, further comprising a rail removably connected to at least one of the first tapered lateral edge and the second tapered lateral edge.

15. The patient support of claim 14, further comprising an interlocking receiver to removably secure the rail to the shell.

16. The patient support of claim 8, further comprising means for engaging a shell attachment to extend the shell in the longitudinal direction.

17. The patient support of claim 16, wherein the engaging means comprises an extension track configured for engagement with a shell attachment.

18. The patient support of claim 17, wherein the extension track is configured to engage a shell attachment having an upper lip spaced from a lower lip by a distance that is approximately equal to a distance between an inner diameter and an outer diameter of the extension track.

* * * * *